(12) United States Patent
Durham et al.

(10) Patent No.: US 6,168,595 B1
(45) Date of Patent: *Jan. 2, 2001

(54) MODULAR INTRAMEDULLARY FIXATION SYSTEM AND INSERTION INSTRUMENTATION

(75) Inventors: Alfred A. Durham, Roanoke, VA (US); Robert L. Daily, Germantown, TN (US); Gregory S. Fandrich, Collierville, TN (US); Lauralan Terrill-Grisoni, Cordova, TN (US); Benjamin R. Shappley, Germantown, TN (US)

(73) Assignee: OrthoMatrix, Inc., Collierville, TN (US)

( * ) Notice: Under 35 U.S.C. 154(b), the term of this patent shall be extended for 0 days.

This patent is subject to a terminal disclaimer.

(21) Appl. No.: 09/467,773

(22) Filed: Dec. 20, 1999

Related U.S. Application Data

(63) Continuation of application No. 08/795,487, filed on Feb. 11, 1997.

(51) Int. Cl.⁷ .................................................. A61B 17/22
(52) U.S. Cl. ............................................. 606/64; 606/104
(58) Field of Search ............................. 606/62, 63, 64, 606/67, 68, 96, 98

(56) References Cited

U.S. PATENT DOCUMENTS

| | | |
|---|---|---|
| 4,776,330 | 10/1988 | Chapman et al. . |
| 4,875,475 | 10/1989 | Comte et al. . |
| 4,877,019 | 10/1989 | Vives . |
| 5,041,114 | 8/1991 | Chapman et al. ............. 606/62 |
| 5,049,151 | 9/1991 | Durham et al. ............... 606/98 |
| 5,100,404 | 3/1992 | Hayes ........................... 606/62 |
| 5,122,141 | 6/1992 | Simpson et al. ............... 606/62 |
| 5,127,913 | 7/1992 | Thomas, Jr. ................... 606/62 |
| 5,190,544 | 3/1993 | Chapman et al. ............. 606/69 |
| 5,458,600 | 10/1995 | Stapert et al. ................. 606/63 |
| 5,478,341 | 12/1995 | Cook et al. ................... 606/62 |
| 5,499,986 | 3/1996 | Dimarco ....................... 606/104 |
| 5,514,415 | 5/1996 | Durham et al. ............... 606/96 |
| 5,562,666 | 10/1996 | Brumfield et al. ............ 606/64 |
| 5,562,667 | 10/1996 | Shuler et al. ................. 606/64 |
| 5,658,287 | 8/1997 | Hofmann et al. ............. 606/63 |

*Primary Examiner*—Michael Buiz
*Assistant Examiner*—David O. Reip
(74) *Attorney, Agent, or Firm*—Garrison, Morris, Haight & Morrow, PLLC

(57) ABSTRACT

An intramedullary nail for use in combination with a proximal bone screw. The nail includes an elongated body having a proximal end and a distal end with a central axis extending between the proximal end and the distal end. The proximal end of the body has a transverse slot therethrough, the transverse slot therethrough with contour for allowing the proximal bone screw to be inserted through the transverse slot and through the proximal end of the body with the longitudinal axis of the proximal bone screw located at an angle to the central axis of the body of the nail within a range between an acute angle on either side of a plane extending transverse to the central axis of the body of the nail.

14 Claims, 16 Drawing Sheets

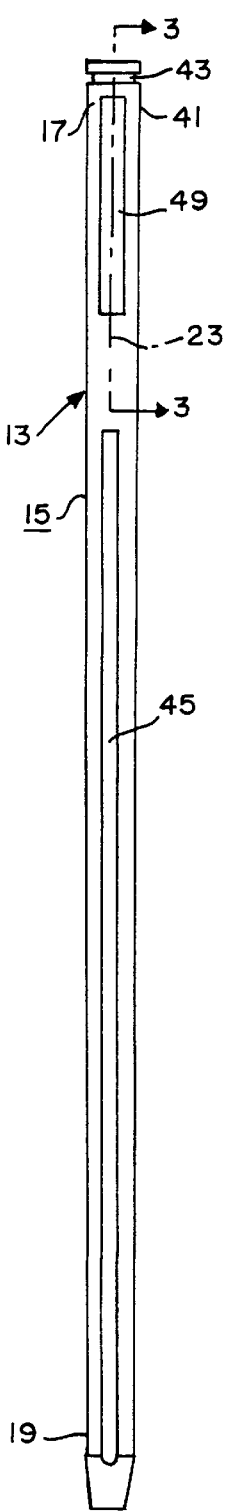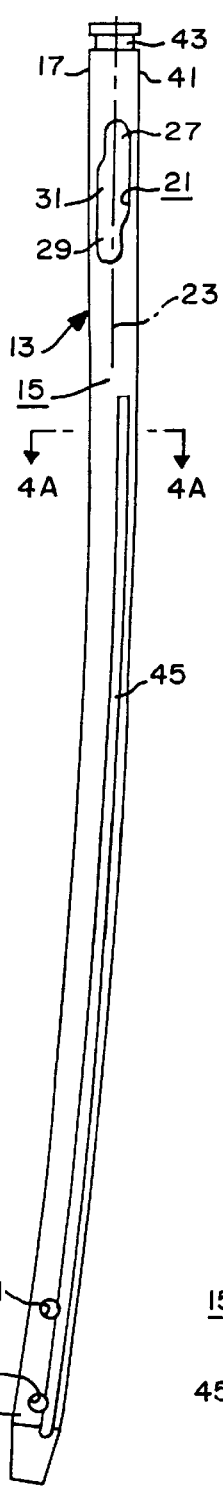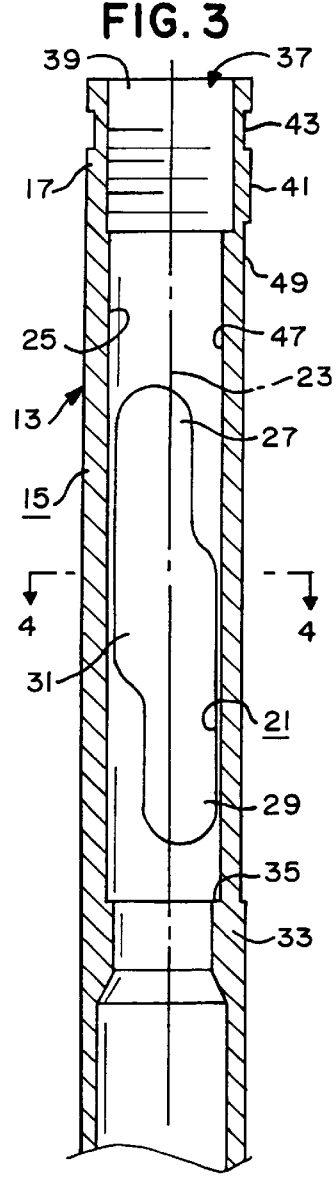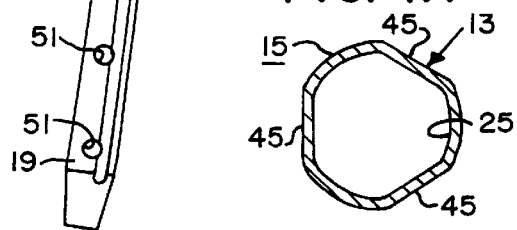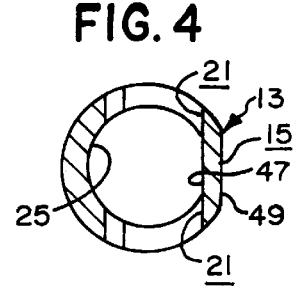

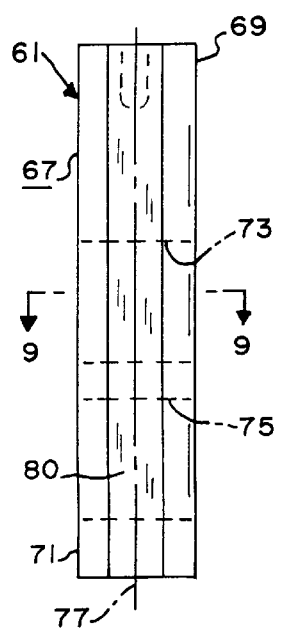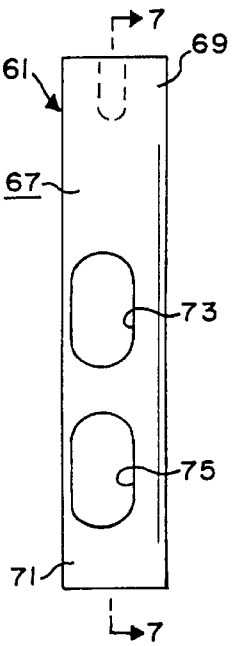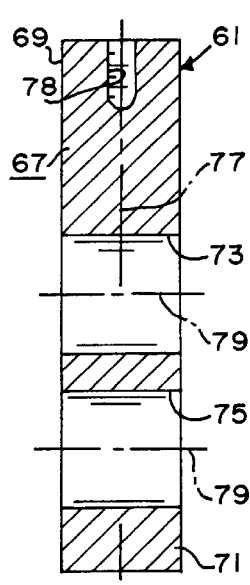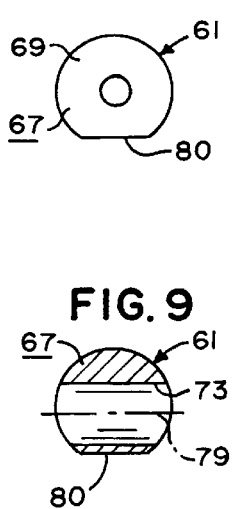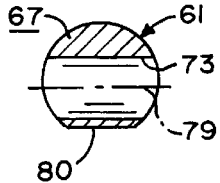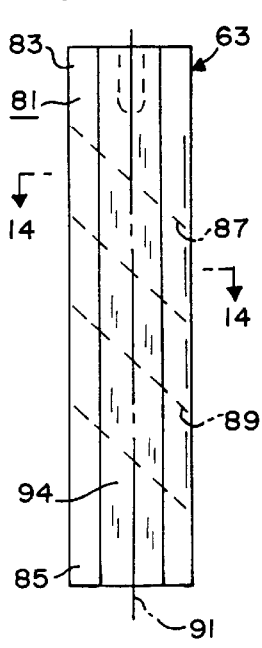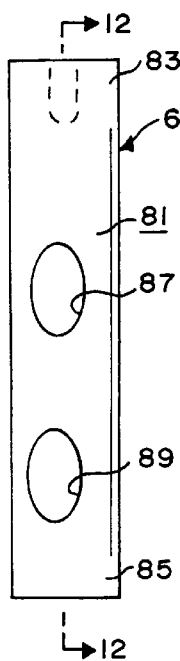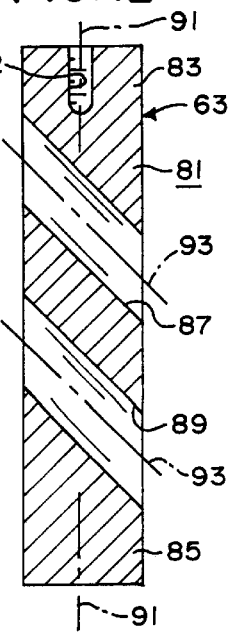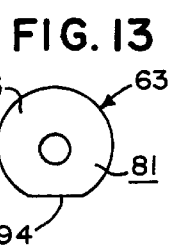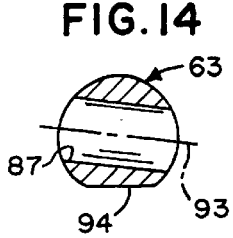

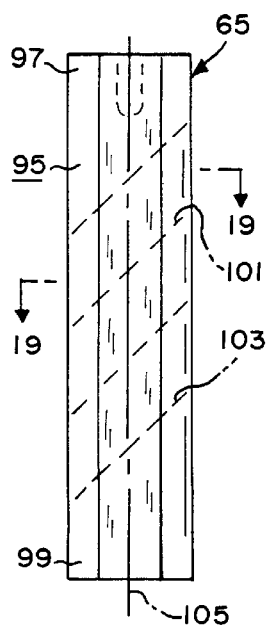
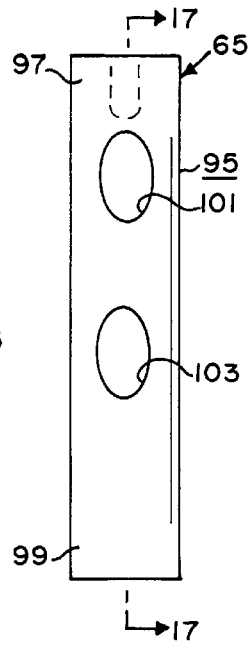
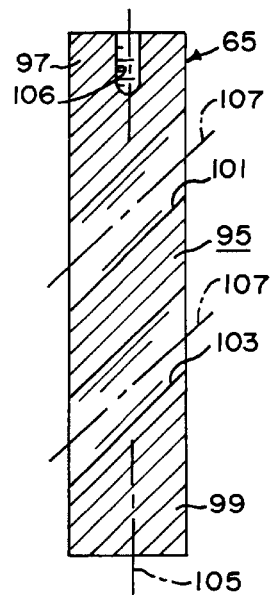
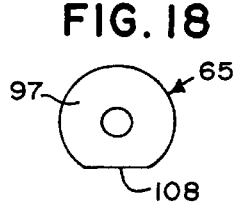
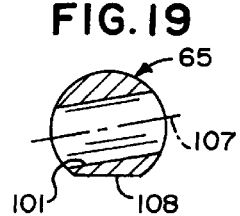
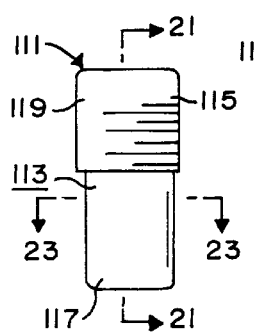
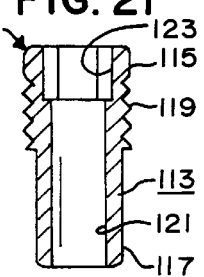
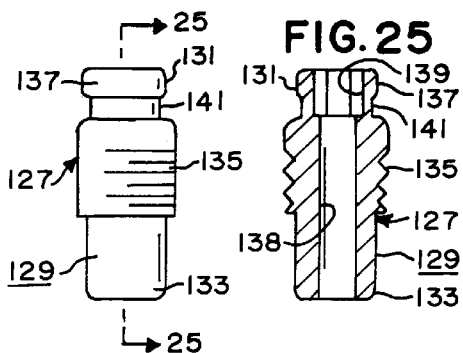
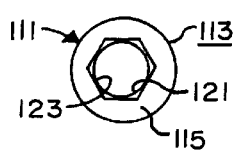
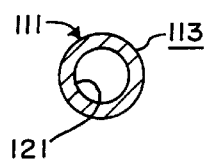
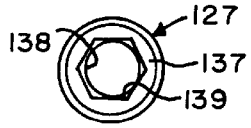

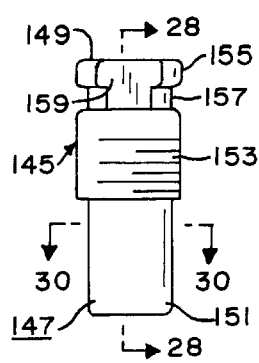
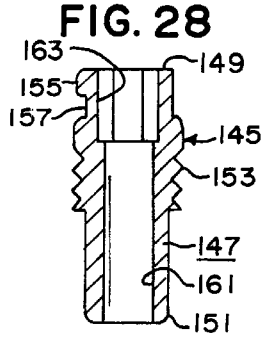
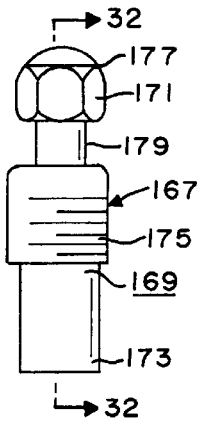
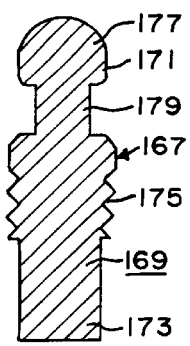
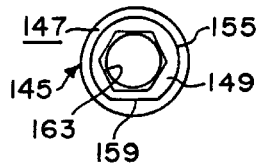
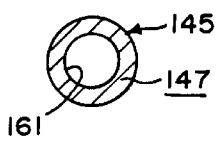
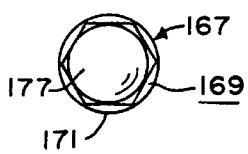
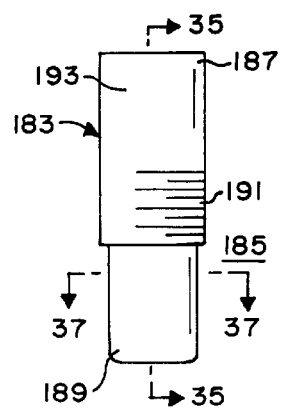
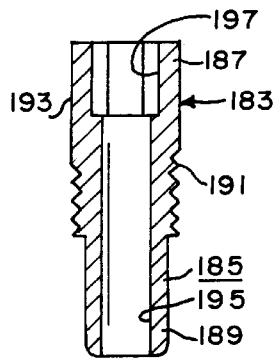
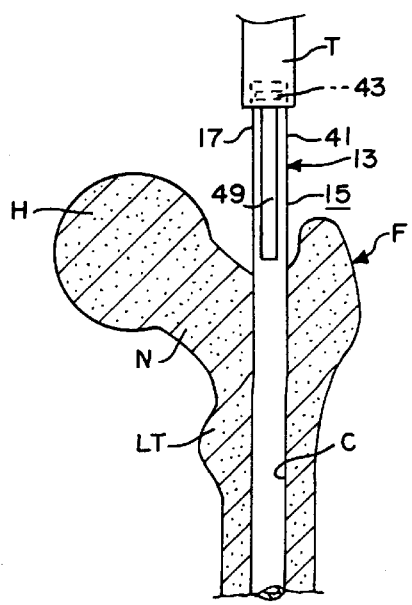
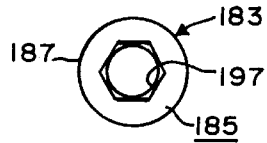
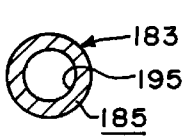

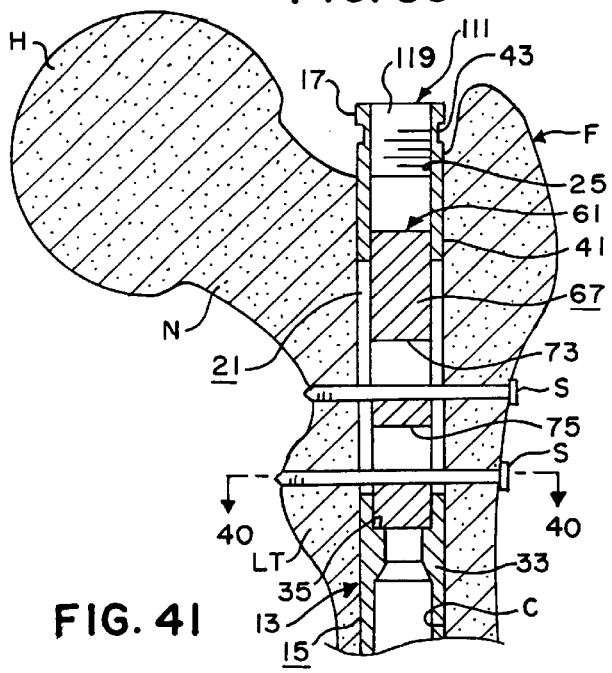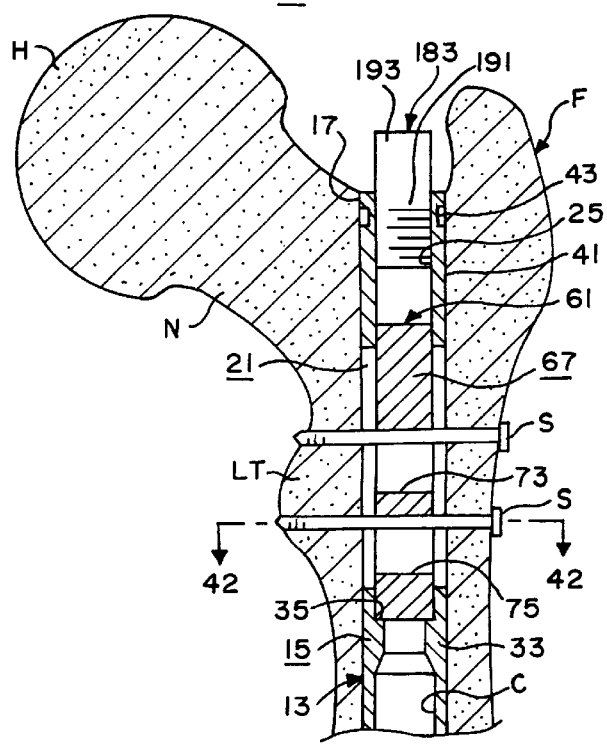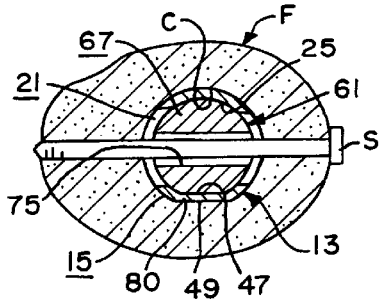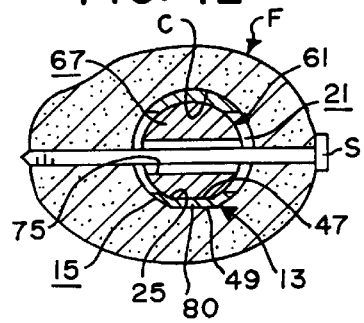

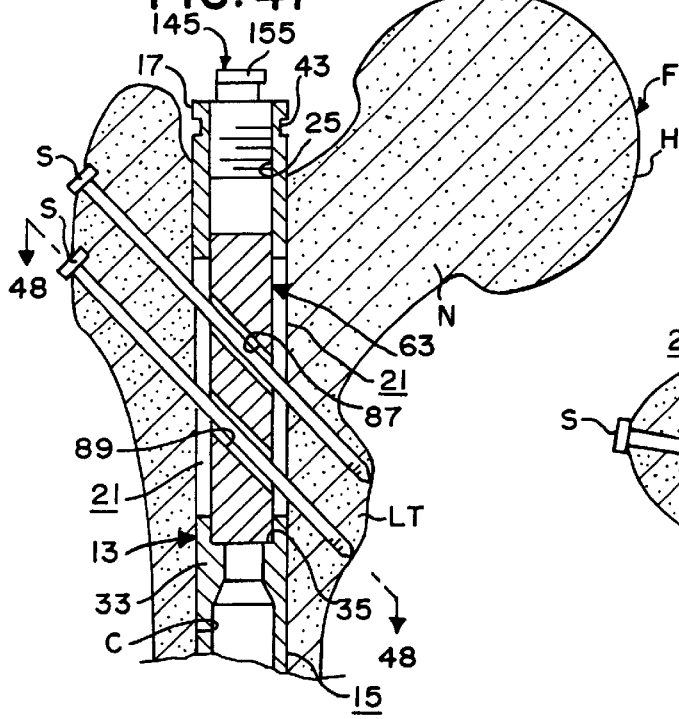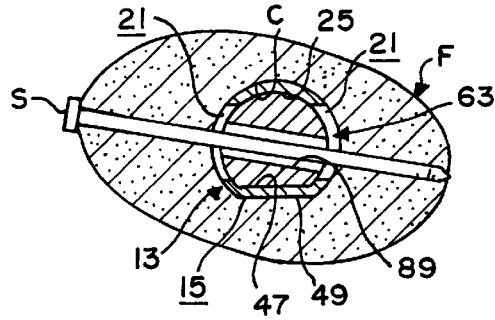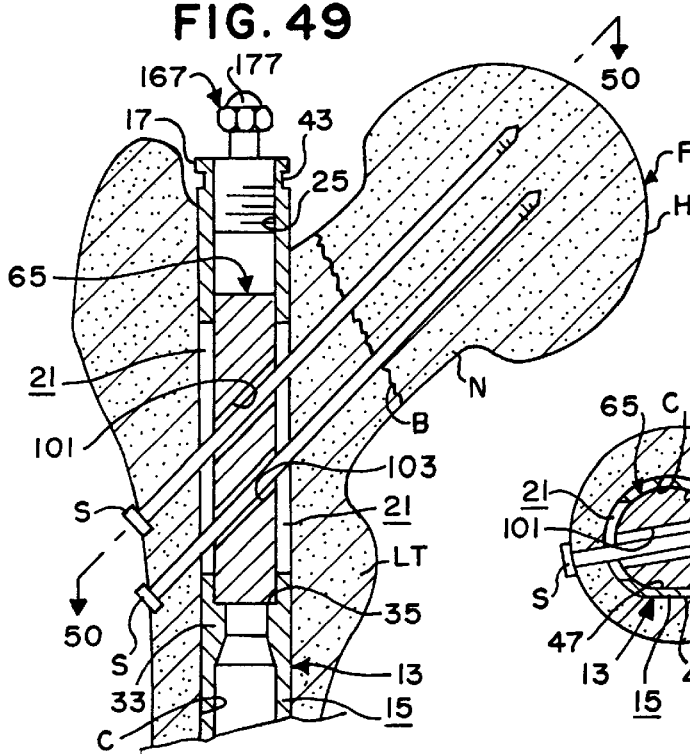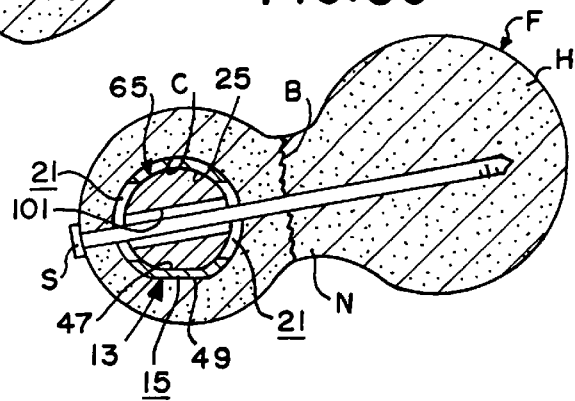

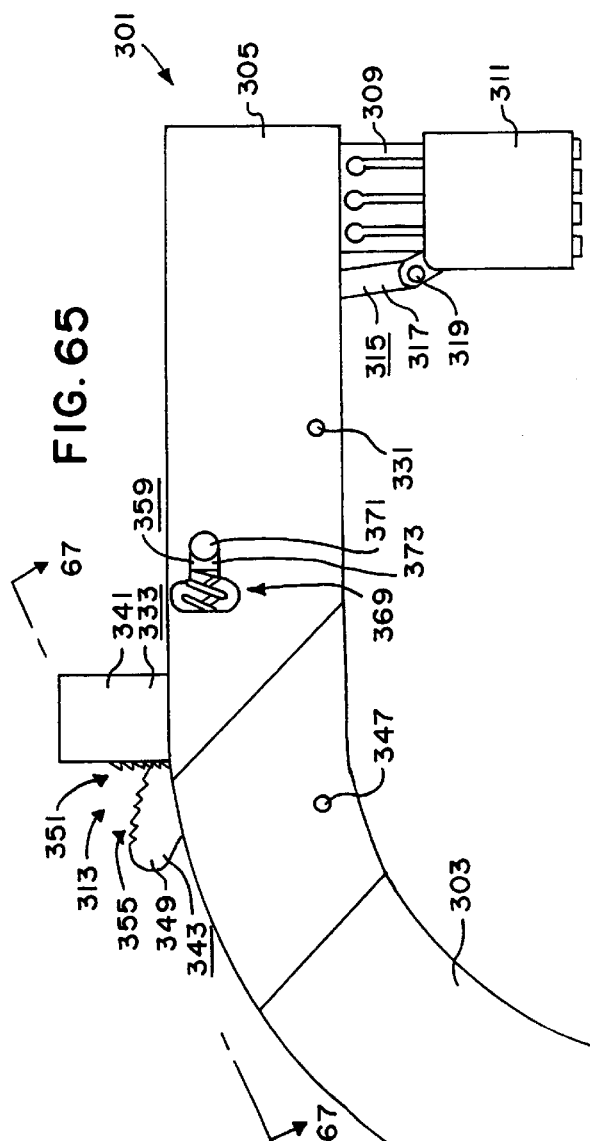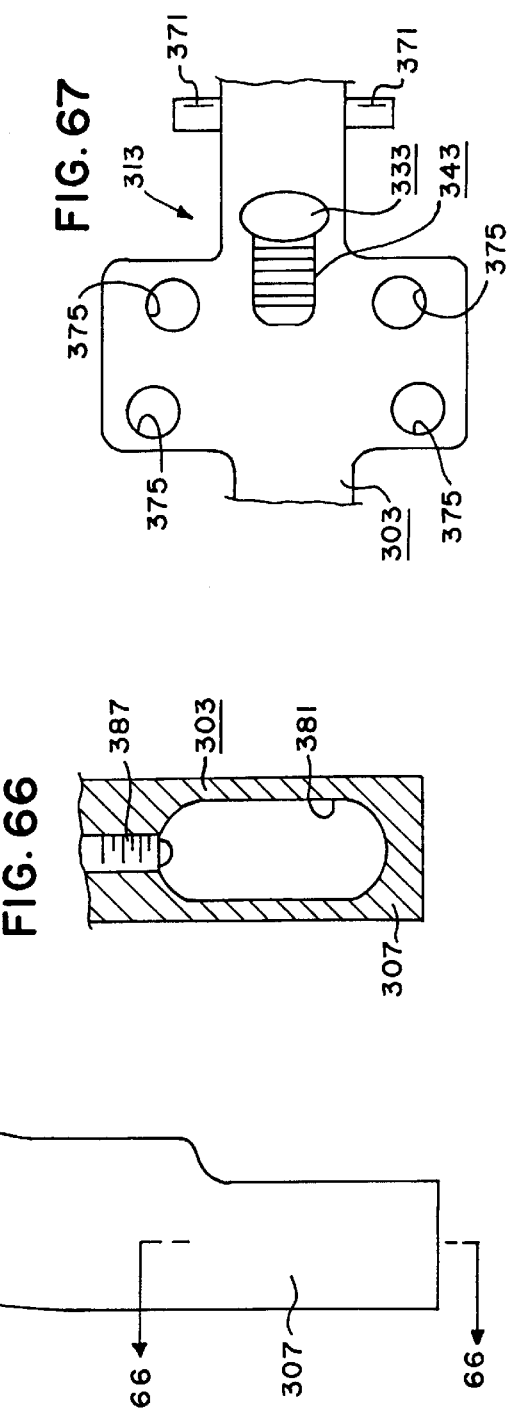

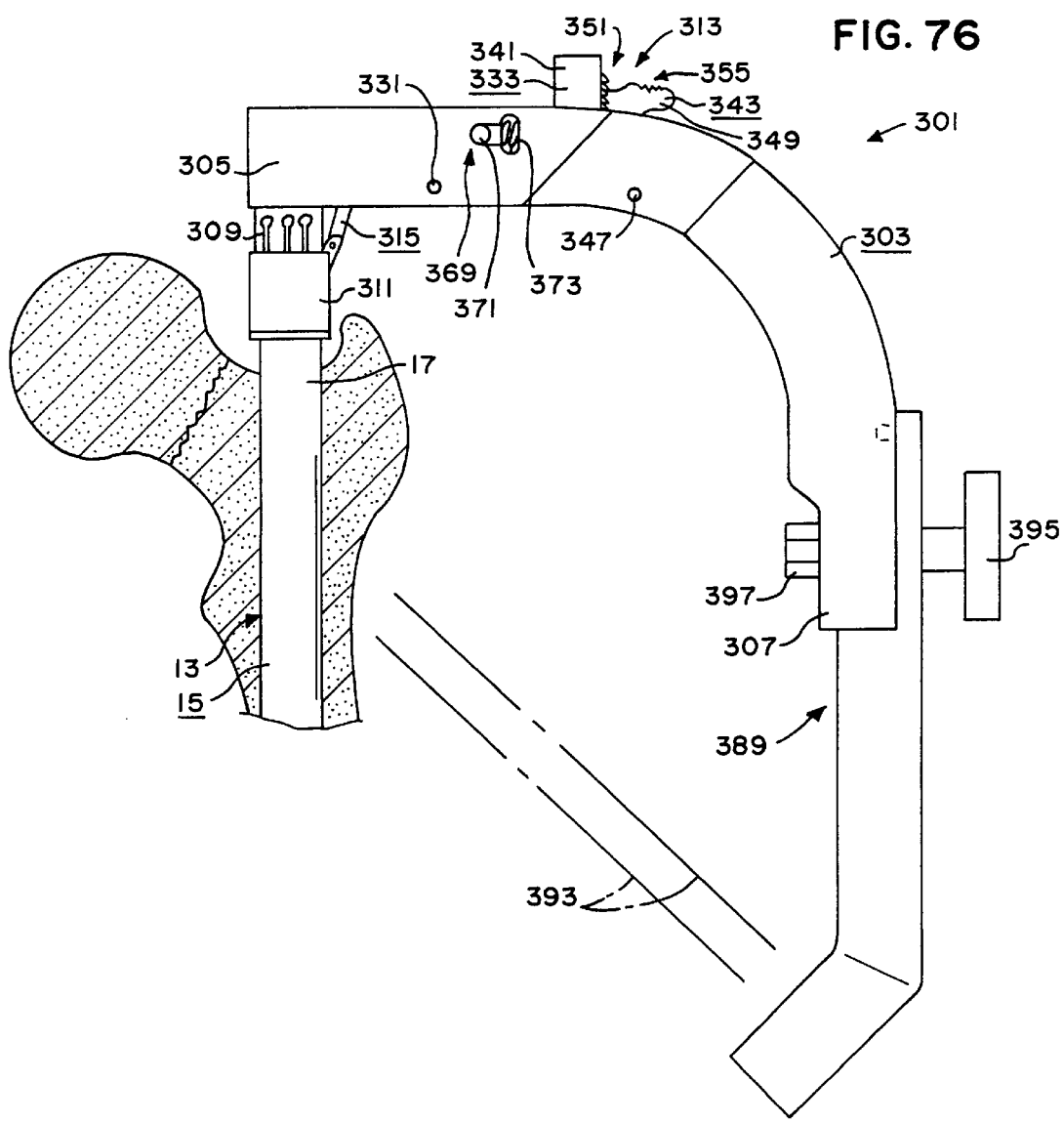

MODULAR INTRAMEDULLARY FIXATION SYSTEM AND INSERTION INSTRUMENTATION

This application is a continuation of Ser. No. 08/795,487 filed Feb. 11, 1997.

BACKGROUND OF THE INVENTION

1. Field of the Invention

The present invention relates, in general, to intramedullary fixation systems and insertion instrumentation, and, more specifically, to a modular intramedullary fixation system and insertion instrumentation therefor.

2. Information Disclosure Statement

A preliminary patentability search produced the following patents which appear to be relevant to the present invention:

Chapman et al., U.S. Pat. No. 4,776,330, issued Oct. 11, 1988, U.S. Pat. No. 5,041,114, issued Aug. 20, 1991, and U.S. Pat. No. 5,190,544, issued Mar. 2, 1993, disclose modular femoral fixation systems for use in the treatment of femoral disorders resulting from injury, disease or congenital defect. Each system includes an elongated intramedullary rod 109 having a pair of transverse bores 115 through the distal end portion thereof and a pair of transverse bores 116 through the proximal end portion thereof (see, in general, FIGS. 19–22 and 25 of U.S. Pat. No. 4,776,330). In the embodiment shown in FIGS. 19 and 20 of U.S. Pat. No. 4,776,330, a diametrical slot 120 is provided at the proximal tip of the intramedullary rod 109 for engagement with appropriate insertion and extraction tools. In the embodiment shown in FIG. 22 of U.S. Pat. No. 4,776,330, a hollow sleeve 131 is detachably secured to the exterior of the proximal end portion of the intramedullary rod 109 by means of a locking screw 135 threaded into an internally-threaded bore 137 in the top of the intramedullary rod 109, thereby effectively increasing the diameter of the proximal end portion of the intramedullary rod 109.

Vives, U.S. Pat. No. 4,877,019, issued Oct. 31, 1989, discloses an intramedullary nail 1 and a beater 20 for use in inserting the intramedullary nail 1. As illustrated in FIGS. 9 and 16–18 of the Vives patent and stated at lines 20–27 of column 3 of the Vives patent, "The beater has a handle body 21 which, at the end facing towards the zone of introduction into the bone, is provided with a threaded portion 20' in which is insertable an adapter 20" onto which the nail can be threaded . . . "

Hayes, U.S. Pat. No. 5,100,404, issued Mar. 31, 1992, discloses an intramedullary nail 31 having an internally-threaded bore in its proximal end for coacting with a bolt construct (i.e., an outer bolt 63 and an inner bolt 64) used for mounting an alignment fixture 81 to the proximal end of the intramedullary nail 31 (see FIGS. 8 and 9 of U.S. Pat. No. 5,100,404), or in combination with a compression nut 62 and a compression washer 64 to provide controlled compression of a fracture (see FIGS. 6 and 7 of U.S. Pat. No. 5,100,404).

Simpson et al., U.S. Pat. No. 5,122,141, issued Jun. 16, 1992, discloses a modular intramedullary nail 10 including a base nail member 12 and an extension nail member 14 adapted to be matingly connected to the base nail member 12 by a "Morse" taper to produce an intramedullary nail of a particular length selected by a surgeon. The extension nail member 14 has a channel 46 therethrough so that a screw 42 can be used to aid the "Morse" taper in joining the base nail member 12 and extension nail member 14 together, and has transverse openings therethrough for receiving bone screws. The proximal end of the extension nail member 14 has a transverse slot 64 thereacross for allowing it to be rotated and for indicating the orientation of the transverse openings through the extension nail member 14.

Thomas, U.S. Pat. No. 5,127,913, issued Jul. 7, 1992, discloses an apparatus and method for implanting an intramedullary rod 12. The intramedullary rod 12 includes a score line 14 at its proximal end for allowing the poles of magnets 24 of an insert member 22 to be aligned with the axis of transverse holes 20 through the distal end of the intramedullary rod 12.

Intramedullary fixation systems are commonly used in treating complex fractures of long bones such as the human femur or tibia. In a typical application, an elongated rod or bar, commonly referred to as a "nail," is inserted into the intramedullary canal of a fractured femur. A typical prior art intramedullary nail may have one or more transverse apertures through the distal end thereof to allow distal bone screws or pins to be screwed or otherwise inserted through the femur and the distal end of the intramedullary nail, thereby securing the distal end of the intramedullary nail to the femur. In addition, a typical intramedullary nail may have one or more apertures through the proximal end thereof to allow proximal bone screws or pins to be screwed or otherwise inserted through the femur and the proximal end of the intramedullary nail, thereby securing the proximal end of the intramedullary nail to the femur. While the distal bone screws or pins may be inserted in a transverse orientation relative to the longitudinal axis of the femur and nail (see, for example, the bone screws 22, 24 in FIGS. 1 and 2 of Simpson et al., U.S. Pat. No. 5,122,141), it may be desired to orient the proximal bone screws or pins in various angles depending on the location of the fracture, etc. For example, to reconstruct and repair a femoral neck fracture, it might be desired to extend one or more proximal bone screws or pins through the proximal end of an intramedullary nail at compound angle substantially equal to the angle of the femoral neck for extending through the femoral neck and into the femoral head (see, for example, the bone screws 58, 60 in FIGS. 1 and 2 of Simpson et al., U.S. Pat. No. 5,122,141). On the other hand, in order to reduce and repair fractures of a femur between the proximal and distal ends thereof, it might be desired to extend one or more bone screws through the proximal end of an intramedullary nail at a downward angle (see, for example, the bone screw 16 in FIG. 1 of Thomas, U.S. Pat. No. 5,127,913).

Nothing in the known prior art discloses or suggests the present invention. More specifically, nothing in the known prior art discloses or suggests an intramedullary nail including an elongated body with a transverse slot through the proximal end thereof having contour for allowing a proximal bone screw to be inserted through the transverse slot and through the proximal end of the body with the longitudinal axis of the proximal bone screw located at an angle to the central axis of the body of the nail within a range between an acute angle on either side of a plane extending transverse to the central axis of the body of the nail.

BRIEF SUMMARY OF THE INVENTION

The present invention provides a modular intramedullary fixation system. A basic concept of the present invention is to provide such a system that provides a truly modular solution for various femoral fractures and the like.

The modular intramedullary fixation system of the present invention includes an intramedullary nail having an elongated body with a transverse slot through the proximal end thereof, the transverse slot having contour for allowing a proximal bone screw to be inserted through the transverse slot and through the proximal end of the body with the longitudinal axis of the proximal bone screw located at an angle to the central axis of the body of the nail within a range between an acute angle on either side of a plane extending transverse to the central axis of the body of the nail. The modular intramedullary fixation system of the present invention may also include various intramedullary nail inserts for insertion into the cavity of the proximal end of the intramedullary nail, and various intramedullary nail caps for securing an insert to the nail.

One object of the present invention is to provide an intramedullary nail as part of a modular intramedullary fixation system that allows more anatomic anteversion and retroversion than any prior art intramedullary nail.

Another object of the present invention is to provide a modular intramedullary fixation system that allows a lot of latitude in selection of proximal bone screw angle and placement, etc.

Another object of the present invention is to provide a modular intramedullary fixation system that is specifically designed to preserve maximum open intramedullary nail canal diameter for optimum use of magnetic positioner instrumentation and methods such as disclosed in Durham et al., U.S. Pat. No. 5,049,151, issued Sep. 17, 1991, and Durham et al., U.S. Pat. No. 5,514,145, issued May 7, 1996.

Another object of the present invention is to provide a modular intramedullary fixation system that incudes a highly versatile nail design so that the necessary inventory of different nails required can be reduced due to the modularity of the nail design.

Another object of the present invention is to provide a modular intramedullary fixation system that allows a combination of solid and hollow intramedullary nails to be used because of the modularity provided.

Another object of the present invention is to provide intramedullary nail insert and cap inserter instrumentation for use in inserting intramedullary nail inserts into the cavity of the proximal end of intramedullary nails, and for securing intramedullary nail caps to intramedullary nails.

Another object of the present invention is to provide such insertion instrumentation that allows both an insert and a cap to be placed during one surgical step, rather than two.

Another object of the present invention is to provide such inserter instrumentation that allows an intramedullary insert to be rotated separately of the intramedullary cap, and also allows placement and threaded tightening of an intramedullary cap without movement of the insert.

Another object of the present invention is to provide such inserter instrumentation that incudes two coaxial shafts, including a inner shaft having a threaded portion or other means for retaining an intramedullary insert which mates with the threaded portion (or other means) on the insert, and including an outer shaft having a hex drive or other means for mating with and tightening or loosening a intramedullary cap, with the inner shaft slidably and freely rotatable within the outer shaft.

Another object of the present invention is to provide an intramedullary nail insertion handle instrument for attachment to the proximal end of the nail and used to position and manipulate the nail during insertion, provide a drill guide holder for the proximal locking screws, guide the distal locking screw locating device, and guide the modular proximal nail insert and nail cap.

Another object of the present invention is to provide such an intramedullary nail insertion handle instrument that attaches to the outside diameter of the nail such that items can be fed down into the nail through the handle.

Another object of the present invention is to provide such an intramedullary nail insertion handle instrument that is easily detached from the nail by a mechanism located outside of the proximal incision.

Another object of the present invention is to provide such an intramedullary nail insertion handle in which portions thereof are made from a radiolucent material so it will not interfere with x-ray images during nail insertion.

Another object of the present invention is to provide such an intramedullary nail insertion handle which is modular so it can be used on both right and left nails in four configurations of proximal screw locking (cross lock static, cross lock dynamic, antegrade, and reconstruction).

BRIEF DESCRIPTION OF THE SEVERAL VIEWS OF THE DRAWINGS

FIG. 1 is a rear or posterior elevational view of an intramedullary nail of the modular intramedullary fixation system of the present invention.

FIG. 2 is a side elevational view of the intramedullary nail of FIG. 1.

FIG. 3 is a sectional view substantially as taken on line 3—3 of FIG. 1 on an enlarged scale.

FIG. 4A is a sectional view substantially as taken on line 4A—4A of FIG. 2 on an enlarged scale.

FIG. 4 is a sectional view substantially as taken on line 4—4 of FIG. 3.

FIG. 5 is a rear or posterior elevational view of a first intramedullary nail insert of the modular intramedullary fixation system of the present invention.

FIG. 6 is a side elevational view of the intramedullary nail insert of FIG. 5.

FIG. 7 is a sectional view substantially as taken on line 7—7 of FIG. 6.

FIG. 8 is a top plan view of the intramedullary nail insert of FIG. 5.

FIG. 9 is a sectional view substantially as taken on line 9—9 of FIG. 5.

FIG. 10 is a rear or posterior elevational view of a second intramedullary nail insert of the modular intramedullary fixation system of the present invention.

FIG. 11 is a side elevational view of the intramedullary nail insert of FIG. 10.

FIG. 12 is a sectional view substantially as taken on line 12—12 of FIG. 11.

FIG. 13 is a top plan view of the intramedullary nail insert of FIG. 10.

FIG. 14 is a sectional view substantially as taken on line 14—14 of FIG. 10.

FIG. 15 is a rear or posterior elevational view of a third intramedullary nail insert of the modular intramedullary fixation system of the present invention.

FIG. 16 is a side elevational view of the intramedullary nail insert of FIG. 15.

FIG. 17 is a sectional view substantially as taken on line 17—17 of FIG. 16.

FIG. 18 is a top plan view of the intramedullary nail insert of FIG. 15.

FIG. 19 is a sectional view substantially as taken on line 19—19 of FIG. 15.

FIG. 20 is a front elevational view of a first intramedullary nail cap of the modular intramedullary fixation system of the present invention.

FIG. 21 is a sectional view substantially as taken on line 21—21 of FIG. 20.

FIG. 22 is a top plan view of the intramedullary nail cap of FIG. 20.

FIG. 23 is a sectional view substantially as taken on line 23—23 of FIG. 20.

FIG. 24 is a front elevational view of a second intramedullary nail cap of the modular intramedullary fixation system of the present invention.

FIG. 25 is a sectional view substantially as taken on line 25—25 of FIG. 24.

FIG. 26 is a top plan view of the intramedullary nail cap of FIG. 24.

FIG. 27 is a front elevational view of a third intramedullary nail cap of the modular intramedullary fixation system of the present invention.

FIG. 28 is a sectional view substantially as taken on line 28—28 of FIG. 27.

FIG. 29 is a top plan view of the intramedullary nail cap of FIG. 27.

FIG. 30 is a sectional view substantially as taken on line 30—30 of FIG. 27.

FIG. 31 is a front elevational view of a fourth intramedullary nail cap of the modular intramedullary fixation system of the present invention.

FIG. 32 is a sectional view substantially as taken on line 32—32 of FIG. 31.

FIG. 33 is a top plan view of the intramedullary nail cap of FIG. 31.

FIG. 34 is a front elevational view of a fifth intramedullary nail cap of the modular intramedullary fixation system of the present invention.

FIG. 35 is a sectional view substantially as taken on line 35—35 of FIG. 34.

FIG. 36 is a top plan view of the intramedullary nail cap of FIG. 34.

FIG. 37 is a sectional view substantially as taken on line 37—37 of FIG. 34.

FIG. 38 is a somewhat diagrammatic, partially sectional view showing the intramedullary nail of the modular intramedullary fixation system of the present invention being inserted into the intramedullary canal of a human femur with the aid of an insertion tool.

FIG. 39 is a somewhat diagrammatic, partially sectional view showing the intramedullary nail of the modular intramedullary fixation system of the present invention inserted into the intramedullary canal of a human femur combined with the first intramedullary nail insert and the first intramedullary nail cap of the modular intramedullary fixation system of the present invention, and with bone screws interlocking the components and femur in a transverse mode with static compression.

FIG. 40 is a sectional view substantially as taken on line 40—40 of FIG. 39.

FIG. 41 is a somewhat diagrammatic, partially sectional view showing the intramedullary nail of the modular intramedullary fixation system of the present invention inserted into the intramedullary canal of a human femur combined with the first intramedullary nail insert and the fifth intramedullary nail cap of the modular intramedullary fixation system of the present invention, and with bone screws interlocking the components and femur in a transverse mode with dynamic compression.

FIG. 42 is a sectional view substantially as taken on line 42—42 of FIG. 41.

FIG. 47 is a somewhat diagrammatic, partially sectional view showing the intramedullary nail of the modular intramedullary fixation system of the present invention inserted into the intramedullary canal of a left human femur combined with the second intramedullary nail insert and the third intramedullary nail cap of the modular intramedullary fixation system of the present invention, and with bone screws interlocking the components and femur in an antegrade mode.

FIG. 48 is a sectional view substantially as taken on line 48—48 of FIG. 47.

FIG. 49 is a somewhat diagrammatic, partially sectional view showing the intramedullary nail of the modular intramedullary fixation system of the present invention inserted into the intramedullary canal of a left human femur combined with the third intramedullary nail insert and the fourth intramedullary nail cap of the modular intramedullary fixation system of the present invention, and with bone screws interlocking the components and femur in a reconstruction mode.

FIG. 50 is a sectional view substantially as taken on line 50—50 of FIG. 49.

FIG. 65 is an elevational view of an intramedullary nail insertion handle instrumentation of the present invention.

FIG. 66 is a sectional view substantially as taken on line 66—66 of FIG. 65.

FIG. 67 is an oblique view substantially as taken on line 67—67 of FIG. 65.

FIG. 76 is a somewhat diagrammatic elevational view of the intramedullary nail insertion handle instrumentation and intramedullary nail assembly of FIG. 74 combined with the reconstruction screw guide assembly of FIG. 71 and with a human femur, with the instrumentation configured for guiding proximal locking screw in reconstruction mode.

DETAILED DESCRIPTION OF THE INVENTION

Figure 43:
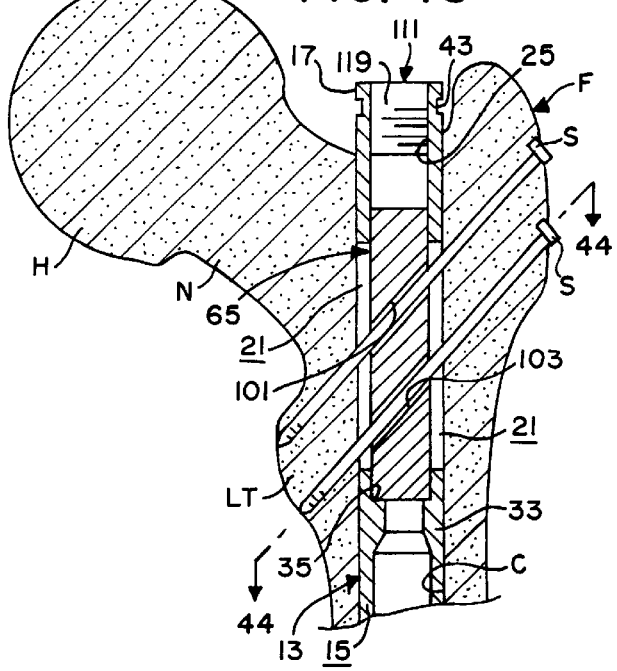
FIG. 43 is a somewhat diagrammatic, partially sectional view showing the intramedullary nail of the modular intramedullary fixation system of the present invention inserted into the intramedullary canal of a right human femur combined with the third intramedullary nail insert and the first intramedullary nail cap of the modular intramedullary fixation system of the present invention, and with bone screws interlocking the components and femur in an antegrade mode.

Preferred embodiments of the modular intramedullary fixation system of the present invention are shown in FIGS. 1–52 and 54–57. The modular intramedullary fixation system of the present invention is especially designed for intramedullary fixation and reconstruction of femoral fractures and the like.

The modular intramedullary fixation system of the present invention includes an intramedullary rod or nail 13 (see, in general, FIGS. 14) for internal fracture fixation of a long bone such as a human femur F (see, in general, FIGS. 38–50). The intramedullary nail 13 is preferably modular. That is, the intramedullary nail 13 is preferably especially designed so that a single intramedullary nail 13 can be used with either a left or right femur F, and to allow multiple configurations of proximal locking including transverse (with static, dynamic, or active dynamic compression), antegrade (with static or active dynamic compression), and reconstruction (with static or active dynamic compression).

The intramedullary nail 13 includes an elongated body 15 consisting, in general, of a hollow shaft, and having a proximal end 17 and a distal end 19. The proximal end 17 of the body 15 of the intramedullary nail 13 has a transverse aperture 21 therethrough. The body 15 of the intramedullary nail 13 has a central or longitudinal axis 23 extending between the proximal and distal ends 17, 19 thereof, and the proximal end 17 thereof has a cavity 25 extending along the central axis 23 toward the distal end 19 thereof. As indicated above, the body 15 preferably consists of a hollow shaft and the cavity 25 preferably extends completely through the body 15, from the proximal end 17 to the distal end 19 thereof as will now be apparent to those skilled in the art.

Figure 51:
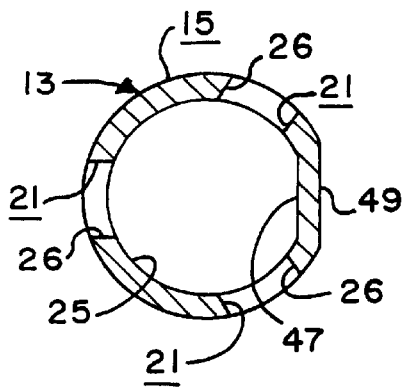
FIG. 51 is an enlarged sectional view similar to FIG. 4 but showing an alternate arrangement of the transverse aperture through the proximal end of the intramedullary nail of the modular intramedullary fixation system of the present invention.
Figure 52:
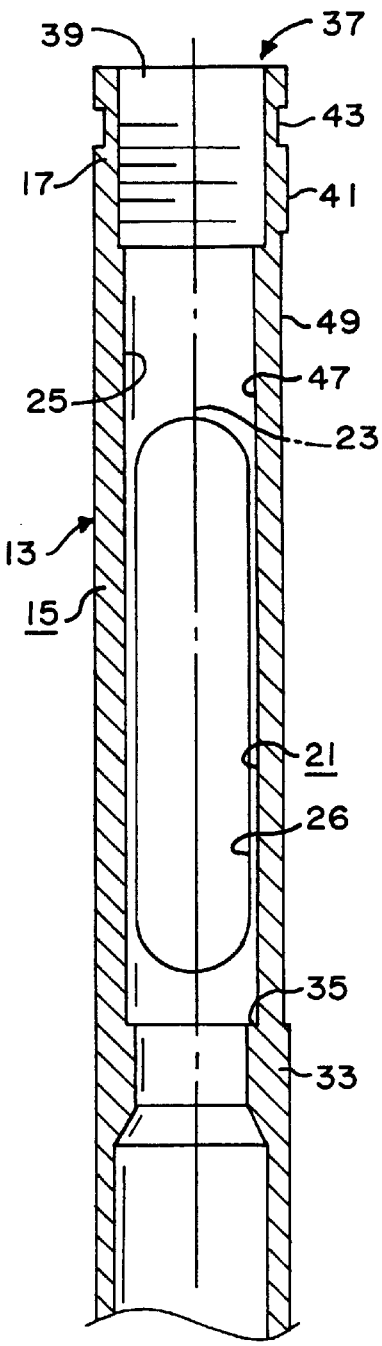
FIG. 52 is a sectional view similar to FIG. 3 but showing another alternate arrangement of the transverse aperture through the proximal end of the intramedullary nail of the modular intramedullary fixation system of the present invention.

The transverse aperture 21 through the proximal end 17 of the body 15 is preferably formed by openings 26 in the wall of the proximal end 17 of the body 15 of the intramedullary nail 13. While the transverse aperture 21 is preferably be formed by a pair of opposed openings 26 as clearly shown in FIG. 4, the transverse aperture 21 may be formed by three or more offset but aligned openings 26 through the wall of the proximal end 17 of the body 15 of the intramedullary nail 13 (see FIG. 51), arranged so that the shaft of a proximal bone screw or the like can extend through any two openings 26 as will now be apparent to those skilled in the art. The transverse aperture 21 through the proximal end 17 of the body 15 (i.e., each opening 26) preferably has a contour with a generally stylized S-shape cross section or cross sectional shape when viewed from one side as shown in FIG. 3. Thus, the contour of the transverse aperture 21 preferably has a proximal end 27, a distal end 29, and a midportion 31 with the proximal and distal ends 27, 29 offset laterally from one another and with the midportion 31 extending between and joining the proximal and distal ends 27, 29. On the other hand, the transverse aperture 21 (i.e., each opening 26) may have a contour with a relatively large oval shape cross section or cross sectional shape as shown generally in FIG. 52.

The body 15 of the intramedullary nail 13 preferably has a protuberance 33 or the like within the cavity 25 thereof at a location adjacent the transverse aperture 21 (e.g., preferably just below the distal end 29 of the transverse aperture 21 as clearly shown in FIG. 3) to form a ledge 35 or the like for reasons which will hereinafter become apparent.

The cavity 25 of the proximal end 17 of the body 15 of the intramedullary nail 13 preferably has an opened mouth 37 with an internally threaded portion 39.

The body 15 of the intramedullary nail 13 has an outer surface 41 and preferably has a transverse groove 43 in the outer surface 41 at the proximal end 17 thereof. The distal end 19 of the body 15 of the intramedullary nail 13 may have a plurality of flats 45 in the outer surface 41 thereof. More specifically, the long distal section or end 19 of the intramedullary nail 13 may have a triangulated circular cross-section, with three spaced flat areas as clearly shown in FIG. 4A, to keep the nail 13 from rotating under torsional loading after being inserted into the intramedullary canal of a femur.

At least a portion of the cavity 25 of the proximal end 17 of the body 15 preferably has contour with a non-circular cross section or cross sectional shape. More specifically, a flat 47 is preferably formed along one side of the contour of the cavity 25 as clearly shown in FIG. 4. The flat 47 preferably extends from the distal end of the internally threaded portion 39 to the ledge 35. A companion flat 49 may be formed on the outer surface 41 of the body 15 directly opposite the wall of the body 15 from the flat 47, and coextensive with the flat 45. The companion flat 49 may be formed as a result of the manufacturing process that forms the flat 47, etc.

Figure 53:
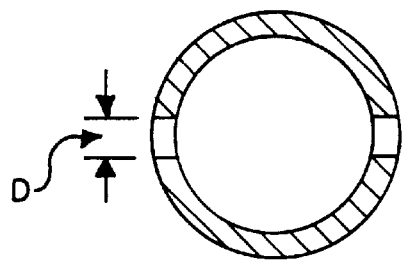
FIG. 53 is an enlarged sectional view through the distal end of a typical prior art intramedullary nail.
Figure 54:
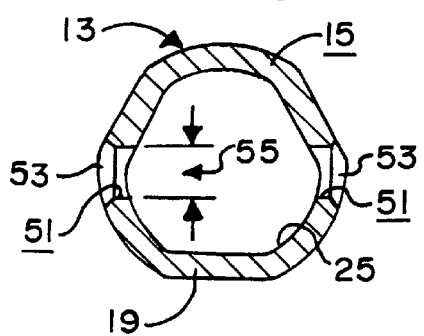
FIG. 54 is an enlarged sectional view substantially as taken on line 54—54 of FIG. 1 but showing an alternate arrangement of the transverse apertures therethrough, etc.

The body 15 of the intramedullary nail 13 preferably has a pair of transverse apertures 51 therethrough adjacent the distal end 19 thereof as shown in FIG. 2. The shape and diameter of each aperture 51 may be specifically designed and sized for allowing easy distal targeting of the intramedullary nail 13. For example, the outer end of each aperture 51 may have an indented or beveled portion 53 as shown in FIG. 54 to act as a guide to for the insertion of bone screws or the like therethrough as will now be apparent to those skilled in the art. Also, while the diameter D of the transverse apertures through the distal end of prior art intramedullary nails as shown in FIG. 53 is typically substantially equal to the diameter of the bone screw to be inserted through such transverse apertures, the diameter 55 of each aperture 51 (see FIG. 54) may be enlarged to allow easy insertion of bone screws or the like therethrough. More specifically, the diameter 55 of each aperture 51 may be approximately 30% larger than the diameter of the bone screws that are intended to be inserted therethrough.

Figure 55:
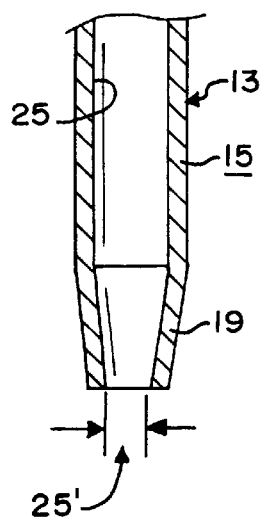
FIG. 55 is an enlarged sectional view substantially as taken on line 55—55 of FIG. 1 with portions thereof omitted for clarity.

In addition, the distal end 19 of the body 15 of the nail 13 is preferably tapered as clearly shown in FIGS. 1, 2 and 55, and the cavity 25 at the distal end 19 of the body 15 is preferably tapered a similar amount so that the cross sectional area or diameter 25' of the cavity 25 at the distal end 19 of the body 15 is reduced as compared to the cross sectional area or diameter thereof at other portions of the body 15 to thereby provide minimum clearance for a guide wire or the like that is typically used to guide such intramedullary nails into prepared intramedullary canals as will now be apparent to those skilled in the art. Such minimum clearance will prevent or hinder any debris from passing into the cavity 25 through the mouth thereof at the distal end 19 of the body 15 as the nail 13 is inserted into the intramedullary canal C.

The long distal section or end 19 of the intramedullary nail 13 may also have an anatomical anterior/posterior bow as shown in FIG. 2 to match the anatomical anterior/posterior curvature of the typical human femur F.

The intramedullary nail 13 may be constructed in various manners and out of various materials as will now be apparent to those skilled in the art. Thus, for example, the intramedullary nail 13 can be forged, machined or otherwise constructed as a one-piece, integral unit out of a medical grade, physiologically acceptable metal such as a stainless steel or the like. Alternatively, the intramedullary nail 13 can be formed from two or more separated pieces, joined together to provide a construct that is as strong as a one-piece, integral unit. The geometry of the intramedullary nail 13 may vary by nail size and length, etc.

The modular intramedullary fixation system of the present invention includes at least one intramedullary nail insert for insertion into the cavity 25 of the proximal end 17 of the body 15 of the intramedullary nail 13. Preferably, however, the modular intramedullary fixation system of the present invention includes a first intramedullary nail insert 61 (see, in general, FIGS. 5–9) for providing left and right transverse proximal locking with static locking or compression (see FIGS. 39 and 40) or dynamic locking or compression (see FIGS. 41 and 42) or, in a modified version, active dynamic compression (see FIG. 57), a second intramedullary nail insert 63 (see, in general, FIGS. 10–14) for providing right reconstruction proximal locking (see FIGS. 45 and 46) and left antegrade proximal locking (see FIGS. 47 and 48), or in a modified version (not shown), active dynamic compression, and a third intramedullary nail insert 65 (see, in general, FIGS. 15–19) for providing right antegrade proximal locking (see FIGS. 43 and 44) and left reconstruction proximal locking (see FIGS. 49 and 50), or in a modified version (not shown), active dynamic compression. Additional intramedullary nail inserts (not shown), having alternative slot geometry, angles, hole alignment, hole diameter, and/or hole spacing, etc., could be provided without changing the geometry of the nail 13.

The intramedullary nail insert 61 includes an elongated body 67 having a proximal end 69 and a distal end 71. The body 67 has at least one and preferably a first transverse aperture 73 and a second transverse aperture 75 therethrough for alignment with the transverse aperture 21 through the proximal end 17 of the body 15 of the intramedullary nail 13 when the intramedullary nail insert 61 is inserted into the cavity 25 of the proximal end 17 of the body 15 of the intramedullary nail 13 as shown in FIGS. 39–42. Each transverse aperture 73, 75 preferably has a contour with a generally slot-shaped cross section or cross sectional shape as shown in FIG. 6. More specifically, the cross sectional shape of the contour of each transverse aperture 73, 75 is preferably taller than wide for reasons which will hereinafter become apparent.

The body 67 has a central axis 77 extending between the proximal and distal ends 69, 71 thereof, and preferably has an internally threaded bore 78 in the proximal end 69 thereof along the central axis 77. Each of the transverse apertures 73, 75 has a central axis 79. The central axis 79 of each of the transverse apertures 73, 75 through the intramedullary nail insert 61 are preferably parallel to one another and perpendicular to the central axis 77 of the body 67 of the intramedullary nail insert 61 as shown in FIG. 7.

The body 67 of the intramedullary nail insert 61 preferably has a contour with a non-circular cross sectional shape (see, in general, FIGS. 8 and 9) that substantially corresponds to the shape of the contour of the cavity 25 of the proximal end 17 of the body 15 of the intramedullary nail 13. More specifically, a flat 80 is preferably formed along the posterior side of the contour of the body 67 as clearly shown in FIGS. 8 and 9. The flat 80 preferably extends the entire length of the body 67. The non-circular cross sectional shapes of the cavity 25 and body 67 thus insure alignment of the transverse apertures 73, 75 through the body 67 of the intramedullary nail insert 61 with the transverse aperture 21 through the proximal end 17 of the body 15 of the intramedullary nail 13 when the intramedullary nail insert 61 is inserted into the cavity 25 of the proximal end 17 of the body 15 of the intramedullary nail 13, coact to define or form means for insuring alignment of the transverse apertures 73, 75 through the body 67 of the intramedullary nail insert 61 with the transverse aperture 21 through the proximal end 17 of the body 15 of the intramedullary nail 13 when the intramedullary nail insert 61 is inserted into the cavity 25 of the proximal end 17 of the body 15 of the intramedullary nail 13, and insure that the insert 61 cannot rotate with respect to the nail 13 when the intramedullary nail insert 61 is inserted into the cavity 25 of the proximal end 17 of the body 15 of the intramedullary nail 13. The central axis 79 through each aperture 73, 75 is preferably parallel to the plane of the flat 80 as clearly indicated in FIG. 9.

Figure 56:
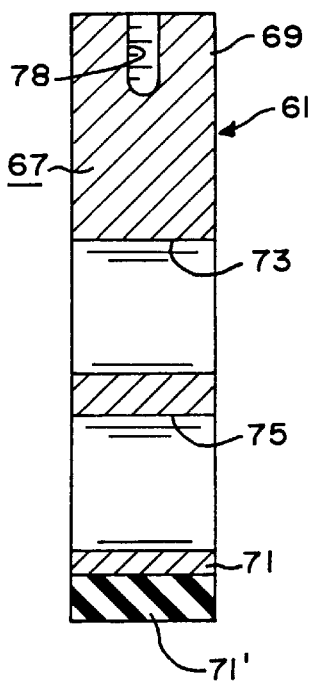
FIG. 56 is a sectional view of a modified version of the first intramedullary nail insert of the modular intramedullary fixation system of the present invention, similar to the version shown in FIGS. 5–9 but having an alternate distal end design thereof.
Figure 57:
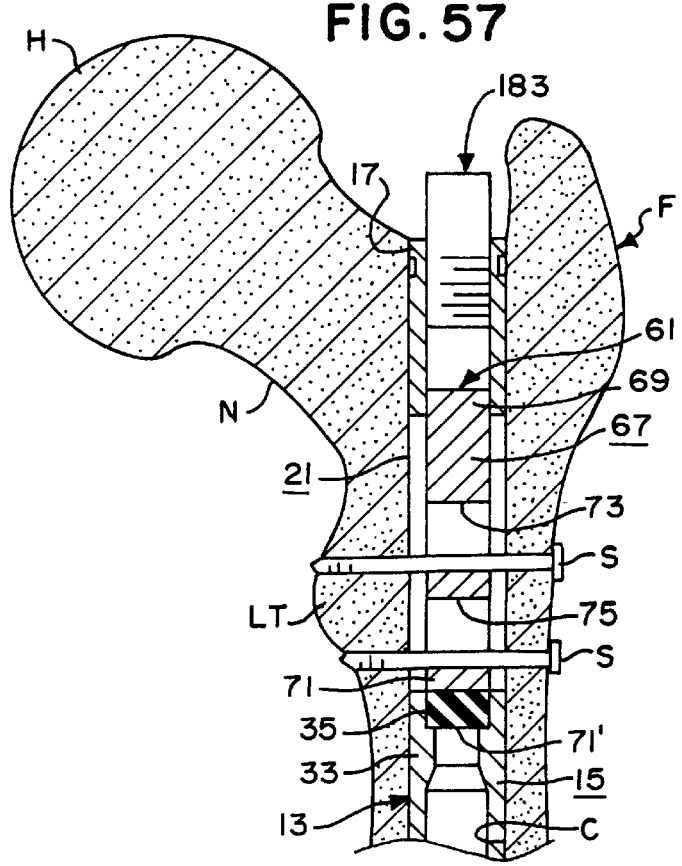
FIG. 57 is a somewhat diagrammatic, partially sectional view similar to FIG. 41, but combined with the modified intramedullary nail insert of FIG. 56 and with bone screws interlocking the components and femur in a transverse mode with active dynamic compression.

The first intramedullary nail insert 61 can be modified specifically for providing active dynamic compression of a fracture or the like merely by having a deformable collar or distal end portion. For example, a modified version of the first intramedullary nail insert 61 is shown in FIGS. 56 and 57 and is identical to the intramedullary nail insert 61 shown in FIGS. 5–9 with the exception that the distal end 71 thereof includes a deformable end portion or collar 71'.

The intramedullary nail insert 63 includes an elongated body 81 having a proximal end 83 and a distal end 85. The body 81 has at least one and preferably a first transverse aperture 87 and a second transverse aperture 89 therethrough for alignment with the transverse aperture 21 through the proximal end 17 of the body 15 of the intramedullary nail 13 when the intramedullary nail insert 63 is inserted into the cavity 25 of the proximal end 17 of the body 15 of the intramedullary nail 13 as shown in FIGS. 45–48. Each transverse aperture 87, 89 preferably has a contour with a generally circular cross sectional shape as shown generally in FIG. 11.

The body 81 has a central axis 91 extending between the proximal and distal ends 83, 85 thereof, and preferably has an internally threaded bore 92 in the proximal end 83 thereof along the central axis 91. Each of the transverse apertures 87, 89 has a central axis 93. The central axis 93 of each of the transverse apertures 87, 89 through the intramedullary nail insert 63 are preferably parallel to one another and angled relative to the central axis 91 of the body 81 of the intramedullary nail insert 63 as shown in FIG. 12.

The body 81 of the intramedullary nail insert 63 preferably has a contour with a non-circular cross sectional shape (see, in general, FIGS. 13 and 14) that substantially corresponds to the shape of the contour of the cavity 25 of the proximal end 17 of the body 15 of the intramedullary nail 13. More specifically, a flat 94 is preferably formed along the posterior side of the contour of the body 81 as clearly shown in FIGS. 13 and 14. The flat 94 preferably extends the entire length of the body 81. The non-circular cross sectional shapes of the cavity 25 and body 81 thus insure alignment of the transverse apertures 87, 89 through the body 81 of the intramedullary nail insert 63 with the transverse aperture 21 through the proximal end 17 of the body 15 of the intramedullary nail 13 when the intramedullary nail insert 63 is inserted into the cavity 25 of the proximal end 17 of the body 15 of the intramedullary nail 13, coact to define or form means for insuring alignment of the transverse apertures 87, 89 through the body 81 of the intramedullary nail insert 63 with the transverse aperture 21 through the proximal end 17 of the body 15 of the intramedullary nail 13 when the intramedullary nail insert 63 is inserted into the cavity 25 of the proximal end 17 of the body 15 of the intramedullary nail 13, and insure that the insert 63 cannot rotate with respect to the nail 13 when the intramedullary nail insert 63 is inserted into the cavity 25 of the proximal end 17 of the body 15 of the intramedullary nail 13. The central axis 93 through each aperture 87, 89 is preferably located at an angle to the plane of the flat 94 as clearly indicated in FIG. 14.

The second intramedullary nail insert 63 can also be modified specifically for providing active dynamic compression of a fracture or the like merely by having a deformable collar or distal end portion (not shown), in the same manner as hereinabove described relative to the modified version of the first intramedullary nail insert 61 shown in FIGS. 56 and 57.

The intramedullary nail insert 65 includes an elongated body 95 having a proximal end 97 and a distal end 99. The body 95 has at least one and preferably a first transverse aperture 101 and a second transverse aperture 103 therethrough for alignment with the transverse aperture 21 through the proximal end 17 of the body 15 of the intramedullary nail 13 when the intramedullary nail insert 65 is inserted into the cavity 25 of the proximal end 17 of the body 15 of the intramedullary nail 13 as shown in FIGS. 43, 44, 49 and 50. Each transverse aperture 101, 103 preferably has a contour with a generally circular cross sectional shape as shown generally in FIG. 11.

The body 95 has a central axis 105 extending between the proximal and distal ends 97, 99 thereof, and preferably has an internally threaded bore 106 in the proximal end 97 thereof along the central axis 105. Each of the transverse apertures 101, 103 has a central axis 107. The central axis 107 of each of the transverse apertures 101, 103 through the intramedullary nail insert 65 are preferably parallel to one another and angled relative to the central axis 105 of the body 95 of the intramedullary nail insert 65 as shown in FIG. 17.

The body 95 of the intramedullary nail insert 65 preferably has a contour with a non-circular cross section or cross sectional shape (see, in general, FIGS. 18 and 19) that substantially corresponds to the shape of the contour of the cavity 25 of the proximal end 17 of the body 15 of the intramedullary nail 13. More specifically, a flat 108 is preferably formed along the posterior side of the contour of the body 95 as clearly shown in FIGS. 18 and 19. The flat 108 preferably extends the entire length of the body 95. The non-circular cross sectional shapes of the cavity 25 and body 95 thus insure alignment of the transverse apertures 101, 103 through the body 95 of the intramedullary nail insert 65 with the transverse aperture 21 through the proximal end 17 of the body 15 of the intramedullary nail 13 when the intramedullary nail insert 65 is inserted into the cavity 25 of the proximal end 17 of the body 15 of the intramedullary nail 13, coact to define or form means for insuring alignment of the transverse apertures 101, 103 through the body 95 of the intramedullary nail insert 65 with the transverse aperture 21 through the proximal end 17 of the body 15 of the intramedullary nail 13 when the intramedullary nail insert 65 is inserted into the cavity 25 of the proximal end 17 of the body 15 of the intramedullary nail 13, and insure that the insert 65 cannot rotate with respect to the nail 13 when the intramedullary nail insert 65 is inserted into the cavity 25 of the proximal end 17 of the body 15 of the intramedullary nail 13. The central axis 107 through each aperture 101, 103 is preferably located at an angle to the plane of the flat 108 as clearly indicated in FIG. 19.

The third intramedullary nail insert 65 can also be modified specifically for providing active dynamic compression of a fracture or the like merely by having a deformable collar or distal end portion (not shown), in the same manner as hereinabove described relative to the modified version of the first intramedullary nail insert 61 shown in FIGS. 56 and 57. The third intramedullary nail inserts 61, 63, 65 may be constructed in various manners and out of various materials as will now be apparent to those skilled in the art. Thus, for example, each intramedullary nail insert 61, 63, 65 can be forged, machined or otherwise constructed as a one-piece, integral unit out of a medical grade, physiologically acceptable metal such as a stainless steel or the like. In order to reduce the possibility of galvanic corrosion, the inserts 61, 63, 65 and nail 13 should be constructed out of similar material. With respect to the modified versions of the inserts 61, 63, 65 for providing active dynamic compression of a fracture or the like, the deformable distal end portion or collar can be molded or otherwise formed out of a biocompatible, deformable plastic, nylon, metal (e.g., a coil spring), etc., and attached to the distal end of the metal proximal end portion, with the overall length and width of the modified inserts the same as the unmodified versions of the inserts. The geometry and size of each intramedullary nail insert 61, 63, 65 can vary to fit the cavity 25 of a specific intramedullary nail 13, etc.

The modular intramedullary fixation system of the present invention preferably includes an intramedullary nail cap for fixing a selected one of the intramedullary nail inserts 61, 63, 65 within the cavity 25 of the proximal end 17 of the body 15 of the intramedullary nail 13.

A first embodiment of the intramedullary nail cap is shown in FIGS. 20–23, 39 and 43, and identified by the numeral 111. The intramedullary nail cap 111 includes an elongated body 113 having a proximal end 115 and a distal end 117. The intramedullary nail cap 111 is especially designed so that the body 113 thereof can be correctly positioned within the cavity 25 of the proximal end 17 of the body 15 of the intramedullary nail 13 after one of the intramedullary nail inserts 61, 63, 65 has been inserted into the cavity 25 of the proximal end 17 of the body 15 of the intramedullary nail 13, with the distal end 117 contacting the proximal end of the body of the respective intramedullary nail inserts 61, 63, 65, and with the proximal end 115 thereof flush with the proximal end 17 of the body 15 of the intramedullary nail 13 as clearly shown in FIGS. 39 and 43. The proximal end 115 of the body 113 of the intramedullary nail cap 111 preferably has an externally threaded portion 119 for screwably mating with the internally threaded portion 39 of the mouth 37 of the cavity 25 of the body 15 of the intramedullary nail 13 to thereby secure the intramedullary nail cap 111 to the intramedullary nail 13. The body 113 may have an aperture 121 extending completely therethrough along the central axis thereof for use with an appropriate insertion tool, and a hexagonal socket 123 is preferably formed in the aperture 121 at the proximal end 115 of the body 113 to allow the intramedullary nail cap 111 to be screwed into the internally threaded portion 39 of the intramedullary nail 13 with the use of a typical hexagonal shaped drive tool or the like. The proximal end 115 of the body 113 is preferably flat and designed so that it will be positioned flush with the proximal end 17 of the body 15 of the intramedullary nail 13 when the intramedullary nail cap 111 is correctly positioned within the cavity 25 of the proximal end 17 of the body 15 of the intramedullary nail 13 to fix one of the intramedullary nail inserts 61, 63, 65 within the cavity 25 of the proximal end 17 of the body 15 of the intramedullary nail 13, as clearly shown in FIGS. 39 and 43.

A second embodiment of the intramedullary nail cap is shown in FIGS. 24–26, and 45, and identified by the numeral 127. The intramedullary nail cap 127 includes an elongated body 129 having a proximal end 131 and a distal end 133. The intramedullary nail cap 127 is especially designed so that the body 129 thereof can be correctly positioned in the cavity 25 of the proximal end 17 of the body 15 of the intramedullary nail 13 after one of the intramedullary nail inserts 61, 63, 65 has been inserted into the cavity 25 of the proximal end 17 of the body 15 of the intramedullary nail 13, with the distal end 133 contacting the proximal end of the body of the respective intramedullary nail inserts 61, 63, 65, and with the proximal end 131 thereof extending above the proximal end 17 of the body 15 of the intramedullary nail 13 as clearly shown in FIG. 45. The body 129 of the intramedullary nail cap 127 preferably has an externally threaded portion 135 positioned generally between the proximal and distal ends 131, 133 thereof for screwably mating with the internally threaded portion 39 of the mouth 37 of the cavity 25 of the body 15 of the intramedullary nail 13 to thereby secure the intramedullary nail cap 127 to the intramedullary nail 13. The body 129 preferably has a head portion 137 at the proximal end 131 thereof above the threaded portion 135, and preferably has an aperture 138 extending completely therethrough along the central axis thereof for use with an appropriate insertion tool, and a hexagonal socket 139 formed in the head portion 137 to allow the intramedullary nail cap 127 to be screwed into the internally threaded portion 39 of the intramedullary nail 13 with the use of a typical hexagonal shaped drive tool or the like. The body 129 preferably has an undercut portion 141 between the head portion 137 and the threaded portion 135 for reasons which will hereinafter become apparent. The intramedullary nail cap 127 is preferably designed so that the head portion 137 and undercut portion 141 will extend above the proximal end 17 of the body 15 of the intramedullary nail 13 when the intramedullary nail cap 127 is correctly positioned within the cavity 25 of the proximal end 17 of the body 15 of the intramedullary nail 13 to fix one of the intramedullary nail inserts 61, 63, 65 within the cavity 25 of the proximal end 17 of the body 15 of the intramedullary nail 13, as clearly shown in FIG. 45.

A third embodiment of the intramedullary nail cap is shown in FIGS. 27–30, and 47, and identified by the numeral 145. The intramedullary nail cap 145 includes an elongated body 147 having a proximal end 149 and a distal end 151. The intramedullary nail cap 145 is especially designed so that the body 147 thereof can be correctly positioned in the cavity 25 of the proximal end 17 of the body 15 of the intramedullary nail 13 after one of the intramedullary nail inserts 61, 63, 65 has been inserted into the cavity 25 of the proximal end 17 of the body 15 of the intramedullary nail 13, with the distal end 151 contacting the proximal end of the body of the respective intramedullary nail inserts 61, 63, 65, and with the proximal end 149 thereof extending above the proximal end 17 of the body 15 of the intramedullary nail 13 as clearly shown in FIG. 47. The body 147 of the intramedullary nail cap 145 preferably has an externally threaded portion 153 positioned generally between the proximal and distal ends 149, 151 thereof for screwably mating with the internally threaded portion 39 of the mouth 37 of the cavity 25 of the body 15 of the intramedullary nail 13 to thereby secure the intramedullary nail cap 145 to the intramedullary nail 13. The body 147 preferably has a head portion 155 at the proximal end 149 thereof above the threaded portion 153, and an undercut portion 157 between the head portion 155 and the threaded portion 153 for reasons which will hereinafter become apparent. A flat 159 may be provided on one side of the head portion 155 and undercut portion 157

(see FIGS. 27 and 29). The body 147 may have an aperture 161 extending completely therethrough along the central axis thereof for use with an appropriate insertion tool, and a hexagonal socket 163 is preferably formed in the aperture 161 at the proximal end 149 of the body 147 to allow the intramedullary nail cap 145 to be screwed into the internally threaded portion 39 of the intramedullary nail 13 with the use of a typical hexagonal shaped drive tool or the like. The intramedullary nail cap 145 is preferably designed so that the head portion 155 and undercut portion 157 will extend above the proximal end 17 of the body 15 of the intramedullary nail 13 when the intramedullary nail cap 145 is correctly positioned within the cavity 25 of the proximal end 17 of the body 15 of the intramedullary nail 13 to fix one of the intramedullary nail inserts 61, 63, 65 within the cavity 25 of the proximal end 17 of the body 15 of the intramedullary nail 13, as clearly shown in FIG. 47.

A fourth embodiment of the intramedullary nail cap is shown in FIGS. 31–33, and 49, and identified by the numeral 167. The intramedullary nail cap 167 includes an elongated body 169 having a proximal end 171 and a distal end 173. The intramedullary nail cap 167 is especially designed so that the body 169 thereof can be correctly positioned in the cavity 25 of the proximal end 17 of the body 15 of the intramedullary nail 13 after one of the intramedullary nail inserts 61, 63, 65 has been inserted into the cavity 25 of the proximal end 17 of the body 15 of the intramedullary nail 13, with the distal end 173 contacting the proximal end of the body of the respective intramedullary nail inserts 61, 63, 65, and with the proximal end 171 thereof extending above the proximal end 17 of the body 15 of the intramedullary nail 13 as clearly shown in FIG. 49. The body 169 of the intramedullary nail cap 167 preferably has an externally threaded portion 175 positioned generally between the proximal and distal ends 171, 173 thereof for screwably mating with the internally threaded portion 39 of the mouth 37 of the cavity 25 of the body 15 of the intramedullary nail 13 to thereby secure the intramedullary nail cap 167 to the intramedullary nail 13. The body 169 preferably has a head portion 177 at the proximal end 171 thereof above the threaded portion 175, and an undercut portion 179 between the head portion 177 and the threaded portion 175 for reasons which will hereinafter become apparent. The head portion 177 preferably has a contour with a hexagonal shaped cross section that defines a bolt-head to allow the intramedullary nail cap 145 to be screwed into the internally threaded portion 39 of the intramedullary nail 13 with the use of a typical wrench or other tool, etc., having a hexagonal-shaped mouth or socket, etc. The intramedullary nail cap 167 is preferably designed so that the head portion 177 and undercut portion 179 will extend above the proximal end 17 of the body 15 of the intramedullary nail 13 when the intramedullary nail cap 167 is correctly positioned within the cavity 25 of the proximal end 17 of the body 15 of the intramedullary nail 13 to fix one of the intramedullary nail inserts 61, 63, 65 within the cavity 25 of the proximal end 17 of the body 15 of the intramedullary nail 13, as clearly shown in FIG. 49.

A fifth embodiment of the intramedullary nail cap is shown in FIGS. 34–37, and 41, and identified by the numeral 183. The intramedullary nail cap 183 includes an elongated body 185 having a proximal end 187 and a distal end 189. The intramedullary nail cap 183 is especially designed so that the body 185 thereof can be correctly positioned in the cavity 25 of the proximal end 17 of the body 15 of the intramedullary nail 13 after one of the intramedullary nail inserts 61, 63, 65 has been inserted into the cavity 25 of the proximal end 17 of the body 15 of the intramedullary nail 13, with the distal end 189 contacting the proximal end of the body of the respective intramedullary nail inserts 61, 63, 65, and with the proximal end 187 thereof extending above the proximal end 17 of the body 15 of the intramedullary nail 13 as clearly shown in FIG. 41. The body 185 of the intramedullary nail cap 183 preferably has an externally threaded portion 191 positioned generally between the proximal and distal ends 187, 189 thereof for screwably mating with the internally threaded portion 39 of the mouth 37 of the cavity 25 of the body 15 of the intramedullary nail 13 to thereby secure the intramedullary nail cap 183 to the intramedullary nail 13. The body 185 preferably has a neck extension portion 193 at the proximal end 187 thereof above the threaded portion 191 for reasons which will hereinafter become apparent. The body 185 may have an aperture 195 extending completely therethrough along the central axis thereof, and a hexagonal socket 197 is preferably formed in the aperture 195 at the proximal end 187 of the body 185 to allow the intramedullary nail cap 183 to be screwed into the internally threaded portion 39 of the intramedullary nail 13 with the use of a typical hexagonal shaped drive tool or the like. However, the intramedullary nail cap 183 could be constructed with a head portion on the neck extension portion 193 similar to the head portion 137 of the second intramedullary nail cap 127, the head portion 155 of the third intramedullary nail cap 145, or the head portion 177 of the fourth intramedullary nail cap 167, etc. The intramedullary nail cap 183 is preferably designed so that the neck extension portion 193 will extend above the proximal end 17 of the body 15 of the intramedullary nail 13 when the intramedullary nail cap 183 is correctly positioned within the cavity 25 of the proximal end 17 of the body 15 of the intramedullary nail 13 to fix one of the intramedullary nail inserts 61, 63, 65 within the cavity 25 of the proximal end 17 of the body 15 of the intramedullary nail 13, as clearly shown in FIG. 41.

The intramedullary nail caps 111, 127, 145, 167, 183 may be constructed in various manners and out of various materials as will now be apparent to those skilled in the art. Thus, for example, each intramedullary nail cap 111, 127, 145, 167, 183 can be forged, machined or otherwise constructed as a one-piece, integral unit out of a medical grade, physiologically acceptable metal such as a stainless steel or the like. In order to reduce the possibility of galvanic corrosion, the caps 111, 127, 145, 167, 183 and nail 13 should be constructed out of similar material. The geometry and size of each intramedullary nail cap 111, 127, 145, 167, 183 can vary to fit the cavity 25 of a specific intramedullary nail 13, etc.

The specific method of intramedullary fixation of the present invention depends on the mode of proximal fixation required or desired, etc. Because the intramedullary nail 13 is truly modular, the initial step in the method of intramedullary fixation of the present invention is to insert the intramedullary nail 13. This step includes typical preoperative planning to estimate proper nail size, bone screw size, etc., and typical surgical approach to expose the proximal femur, etc. The intramedullary canal C of the femur F can be prepared in any typical manner, such as by reaming to desired size, etc. The intramedullary nail 13 can then be inserted into the prepared intramedullary canal C by using a typical insertion tool T such as a slap hammer or the like (see FIG. 38). However, the insertion tool T is preferably adapted to engage and be retained by the transverse groove 43 in the outer surface 41 of the body 15 of the intramedullary nail 13. The transverse groove 43 thus defines and serves as a retaining means for proximal insertion instruments and tools, etc. The intramedullary nail 13 is inserted into the intramedullary canal C to the depth desired by the surgeon. It is normally desired that the proximal end 17 of the intramedullary nail 13 extend above the surface of the femur F when the intramedullary nail 13 is fully inserted into the intramedullary canal C. However, if the anatomy of the femur F is such that the proximal end 17 of the intramedullary nail 13 will sink below the surface of the femur F when properly inserted into the intramedullary canal C, the fifth intramedullary nail cap 183 should be used as shown in FIG. 41 to effectively extend the length of the nail 13 and position the proximal end of the intramedullary nail 13 above the surface of the femur F. The fifth intramedullary nail cap 183 can be provided in various lengths to effectively extend the length of the intramedullary nail 13 various amounts as will now be apparent to those skilled in the art.

In any event, once the intramedullary nail 13 has been properly inserted in the intramedullary canal C, the distal end 19 thereof is locked to the femur F by inserting distal bone screws through the femur F and the transverse apertures 51 of the distal end 19 of the intramedullary nail 13. While this distal locking step can be performed by any method now apparent to those skilled in the art, the present invention is especially adapted to allow the distal bone screws to be inserted using the magnetic positioner instrumentation and methods disclosed in Durham et al., U.S. Pat. No. 5,049,151, issued Sep. 17, 1991, and Durham et al., U.S. Pat. No. 5,514,145, issued May 7, 1996, both incorporated herein by reference. For example, by allowing the insertion instrumentation and tools to be attached to the exterior of the intramedullary nail 13 via the transverse groove 43, the interior of the intramedullary nail 13 (e.g., the bore or cavity 25) is free of such retaining means and the diameter thereof is maximized, thereby providing the required clearance inside the intramedullary nail 13 for the distal targeting options (e.g., target magnets for positioning inside intramedullary nails adjacent the distal ends thereof) taught by Durham et al., U.S. Pat. No. 5,049,151, and Durham et al., U.S. Pat. No. 5,514,145.

Once the distal end 19 of the intramedullary nail 13 is interlocked with the femur F, one of the intramedullary nail inserts 61, 63, 65, etc., is selected, depending on the type of proximal locking mode desired and whether a right or left femur is being fixed, etc.

First, when it is desired to provide transverse proximal locking of either a right or left femur F as shown in FIGS. 39–42, a first intramedullary nail insert 61 is inserted into the cavity 25 in the proximal end 17 of the body 15 of the distally interlocked intramedullary nail 13. Because of the coaction between the flat 47 within the cavity 25 and the flat 80 on the body 67 of the intramedullary nail insert 61, proper alignment of the apertures 73, 75 through the intramedullary nail insert 61 and the transverse aperture 21 through the intramedullary nail 13 is insured. In addition to eliminating the possibility that the insert 61 could be placed incorrectly, the coaction of the flats 47, 80 keeps the insert 61 from rotating within the nail 13. The distal end 71 of the body 67 of the intramedullary nail insert 61 will rest or stop on the ledge 35 within the cavity 25 of the intramedullary nail 13. The ledge 35 thus acts as a stop means and a force transmission member, transferring force from the insert 61 to the distal end 19 of the nail 13. Next, one of the intramedullary nail caps 111, 127, 145, 167, 183 is selected, depending upon the surgeon's discretion, and screwed into the proximal end 17 of the intramedullary nail 13 to secure the intramedullary nail insert 61 within the cavity 25 of the intramedullary nail 13. For example, the first intramedullary nail cap 111 is shown in FIG. 39, with the roof or top of the cap 111 flush with the top or proximal end 17 of the nail 13. The fifth intramedullary nail cap 183 is shown in FIG. 41, effectively extending the length of the nail 13. The selected cap is merely screwed into the cavity 25 in the top of the nail 13, and the distal end of the selected cap contacts the top or proximal end 69 of the insert 61. The caps thus ensures contact between the insert 61 and the ledge 35 of the nail 13, and 11 ensures that the insert 61 is completely seated and contacting the nail 13, and that the insert 61 cannot back out of or move within the nail 13. However, it should be noted that the selected insert and cap can, if desired, be inserted into and attached to the nail 13 together, as an integral unit, etc. If extraction of the nail 13 becomes desirable, the respective flush top caps 111, 183 can be removed from the nail 13, and a removal instrument with a slap hammer attachment or the like screwed into or otherwise attached to the proximal end 17 of the nail 13 to extract the nail 13 as will now be apparent to those skilled in the art, etc. If, on the otherhand, one of the caps 127, 145, 167 having a head portion and an undercut portion is attached to the proximal end 17 of the nail 13, in order to extract the nail 13, that cap 127, 145, 167 is left attached to the nail 13, and a removal instrument with a slap hammer attachment or the like having a hook or claw, etc., for hooking around the undercut portion of the cap or otherwise engaging the head portion of the cap, can be used to extract the nail 13 as will now be apparent to those skilled.

Next, at least one and preferably a spaced pair of proximal bone screws S are inserted horizontally through the lateral bone cortex of the femur F, through the aperture 21 in the proximal end 17 of the body 15 of the nail 13, through the apertures 73, 75 in the body 67 of the insert 61, and back out the medial cortex of the femur F as clearly shown in FIGS. 39 and 41. Depending upon whether more compression is desired across the fracture site, etc., the bone screws S can be placed in the insert 61 in the proximal position as shown in FIG. 41, or in the distal position as shown in FIG. 39. More specifically, the actual location or position of the bone screws S in the respective slot-shaped apertures 73, 75 will determine whether the fixation compression mode is static or dynamic (or active dynamic when using modified versions of the inserts). Thus, by inserting the bone screws S along the distal or bottom end of each aperture 73, 75 as clearly shown in FIG. 39, the fixation compression mode will be static, and the fracture will be locked into the position achieved by reduction. However, by inserting the bone screws S along the proximal or top end of each aperture 73, 75 as clearly shown in FIG. 41, the fixation compression mode will be dynamic, and the fracture will be allowed to settle via relative screw shifting toward the distal end of each aperture 73, 75 upon weight bearing. Further, by using the modified version of the first intramedullary nail insert 61 as shown in FIGS. 56 and 57, and by inserting the bone screws S along the distal or bottom end of each aperture 73, 75 as clearly shown in FIG. 57, the fixation compression mode will be active dynamic, and the fracture will be allowed to settle via controlled compression or deformation of the deformable portion or collar 71' upon weight bearing or upon manual compression by the surgeon interoperatively by screwing the selected cap further into the nail 13.

It should be noted that actual insertion of the proximal bone screws S can be performed in any typical manner using, for example, various proximal screw guides and the like for targeting the precise location thereof, etc., as will now be apparent to those skilled in the art. The surgical site can then be closed and post-operative care can proceed in the normal manner now apparent to those skilled in the art.

Figure 44:
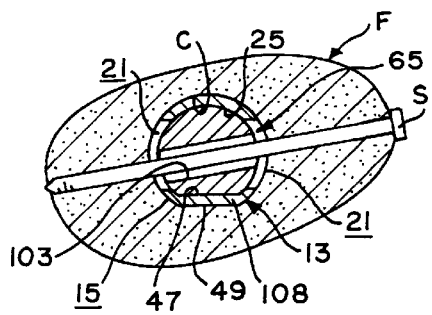
FIG. 44 is a sectional view substantially as taken on line 44—44 of FIG. 43.

Second, when it is desired to provide antegrade proximal locking of a right femur F as shown in FIGS. 43 and 44, a third intramedullary nail insert 65 is inserted into the cavity 25 in the proximal end 17 of the body 15 of the distally interlocked intramedullary nail 13. Because of the coaction between the flat 47 within the cavity 25 and the flat 108 on the body 95 of the intramedullary nail insert 65, proper alignment of the apertures 101, 103 through the intramedullary nail insert 65 and the transverse aperture 21 through the intramedullary nail 13 is insured. In addition to eliminating the possibility that the insert 65 could be placed incorrectly, the coaction of the flats 47, 108 keeps the insert 65 from rotating within the nail 13. The distal end 99 of the body 95 of the intramedullary nail insert 65 will rest or stop on the ledge 35 within the cavity 25 of the intramedullary nail 13. The ledge 35 thus acts as a force transmission member, transferring force from the insert 65 to the distal end 19 of the nail 13. Next, one of the intramedullary nail caps 111, 127, 145, 167, 183 is selected, depending upon the surgeon's discretion, and screwed into the proximal end 17 of the intramedullary nail 13 to secure the intramedullary nail insert 65 within the cavity 25 of the intramedullary nail 13. For example, the first intramedullary nail cap 111 is shown in FIG. 43, with the roof or top of the cap 111 flush with the top or proximal end 17 of the nail 13. The selected cap is merely screwed into the cavity 25 in the top of the nail 13, and the distal end of the selected cap contacts the top or proximal end 69 of the insert 65. The selected cap thus ensures contact between the insert 65 and the ledge 35 of the nail 13, and ensures that the insert 65 is completely seated and contacting the nail 13, and that the insert 65 cannot back out of or move within the nail 13. However, it should be noted that the selected insert and cap can, if desired, be inserted into and attached to the nail 13 together, as an integral unit, etc. If extraction of the nail 13 becomes desirable, the respective flush top cap 111 can be removed from the nail 13, and a removal instrument with a slap hammer attachment or the like screwed into or otherwise attached to the proximal end 17 of the nail 13 to extract the nail 13 as will now be apparent to those skilled in the art, etc.

Next, at least one and preferably a spaced pair of proximal bone screws S are inserted at an angle through the lateral bone cortex of the femur F, through the aperture in the proximal end 17 of the body 15 of the nail 13, through the apertures 101, 103 in the body 95 of the insert 65, and back out the medial cortex of the femur F as clearly shown in FIGS. 43 and 44. In the antegrade mode, the bone screws S travel down through the proximal femur F. Because of the built-in angled orientation of the apertures 101, 103 in the body 95 of the insert 65, the antegrade locking screws S are typically allowed to travel through the lesser trochanter LT of the femur F as clearly shown in FIG. 43 to increase bone purchase. The angled orientation of the central axes 107 of the apertures 101, 103 with respect to the plane of the flat 108 of the body 95 of the insert 65 also provides a degree of retroversion to the construct as clearly shown in FIG. 44. It should be noted that actual insertion of the proximal bone screws S can be performed in any typical manner using, for example, various proximal screw guides and the like for targeting the precise location thereof, etc., as will now be apparent to those skilled in the art. The surgical site can then be closed and post-operative care can proceed in the normal manner now apparent to those skilled in the art.

Figure 45:
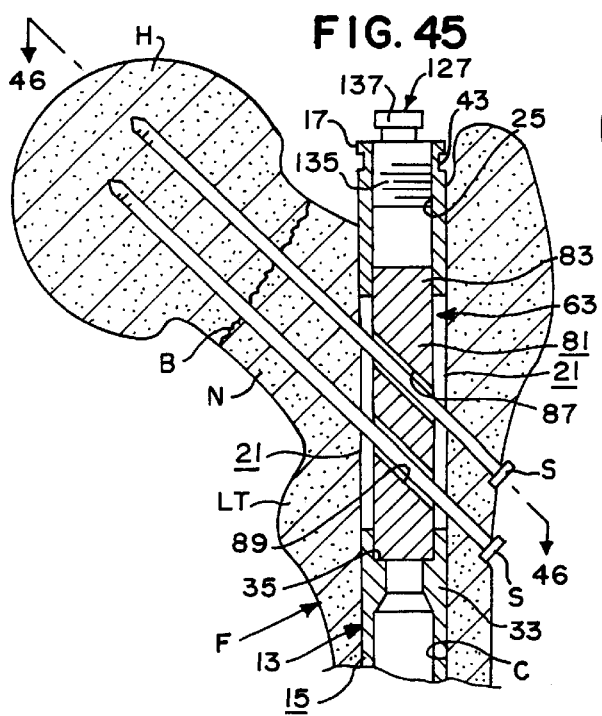
FIG. 45 is a somewhat diagrammatic, partially sectional view showing the intramedullary nail of the modular intramedullary fixation system of the present invention inserted into the intramedullary canal of a right human femur combined with the second intramedullary nail insert and the second intramedullary nail cap of the modular intramedullary fixation system of the present invention, and with bone screws interlocking the components and femur in a reconstruction mode.
Figure 46:
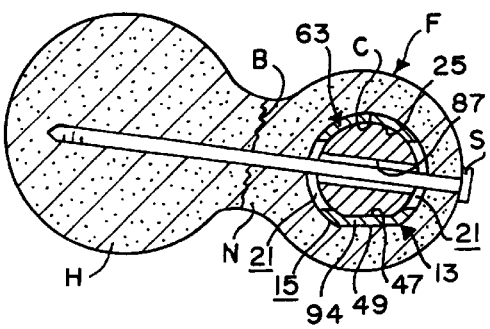
FIG. 46 is a sectional view substantially as taken on line 46—46 of FIG. 45.

Third, when it is desired to provide reconstruction proximal locking of a right femur F to allow repair of femoral neck fractures as shown in FIGS. 45 and 46, a second intramedullary nail insert 63 is inserted into the cavity 25 in the proximal end 17 of the body 15 of the distally interlocked intramedullary nail 13. Because of the coaction between the flat 47 within the cavity 25 and the flat 94 on the body 81 of the intramedullary nail insert 63, proper alignment of the apertures 87, 89 through the intramedullary nail insert 65 and the transverse aperture 21 through the intramedullary nail 13 is insured. In addition to eliminating the possibility that the insert 63 could be placed incorrectly, the coaction of the flats 47, 94 keeps the insert 63 from rotating within the nail 13. The distal end 85 of the body 81 of the intramedullary nail insert 63 will rest or stop on the ledge 35 within the cavity 25 of the intramedullary nail 13. The ledge 35 thus acts as a force transmission member, transferring force from the insert 63 to the distal end 19 of the nail 13. Next, one of the intramedullary nail caps 111, 127, 145, 167, 183 is selected, depending upon the surgeon's discretion, and screwed into the proximal end 17 of the intramedullary nail 13 to secure the intramedullary nail insert 63 within the cavity 25 of the intramedullary nail 13. For example, a second intramedullary nail cap 127 is shown in FIG. 45, with the head portion 137 and undercut portion 141 of the cap 127 extending above the top or proximal end 17 of the nail 13 to be used to help extract the nail 13 from the femur F if extraction becomes desirable. More specifically, a removal instrument with a slap hammer attachment or the like having a hook or claw, etc., for hooking around the undercut portion 141 of the cap 127 or otherwise engaging the head portion 137, can be used to extract the nail 13 as will now be apparent to those skilled in the art. The selected cap is merely screwed into the cavity 25 in the top of the nail 13, and the distal end of the selected cap contacts the top or proximal end 83 of the insert 63. The selected cap thus ensures contact between the insert 63 and the ledge 35 of the nail 13, and ensures that the insert 63 is completely seated and contacting the nail 13, and that the insert 63 cannot back out of or move within the nail 13. However, it should be noted that the selected insert and cap can, if desired, be inserted into and attached to the nail 13 together, as an integral unit, etc.

Next, at least one and preferably a spaced pair of proximal bone screws S are inserted at an angle through the lateral bone cortex of the femur F, through the aperture 21 in the proximal end 17 of the body 15 of the nail 13, through the apertures 87, 89 in the body 81 of the insert 63, through the neck N of the femur F across any fracture or break B therein, and into the head H of the femur F as clearly shown in FIGS. 45 and 46. Thus, in this reconstruction mode, the bone screws S are placed through the nail 13 and insert 63, and travel through the femoral neck N and into the femoral head H. In order to stay centered within the femoral neck N (especially when using a reconstruction bone screw S having a length of 115 millimeters or so), the built-in angled orientation of the apertures 87, 89 in the body 81 of the insert 63, cause the reconstruction locking screws S to travel through the neck N of the femur F at an anatomical femoral neck angle of approximately 135° and an anteversion angle of approximately 12°. The angled orientation of the central axes 93 of the apertures 87, 89 with respect to the plane of the flat 94 of the body 81 of the insert 63 provides the degree of anteversion to the construct as clearly shown in FIG. 46, while the angled orientation of the central axes 93 of the apertures 87, 89 with respect to the central axis 91 of the body 81 of the insert 63 provides the anatomical femoral neck angle to the construct as clearly shown in FIG. 45. It should be noted that actual insertion of the proximal bone screws S can be performed in any typical manner using, for example, various proximal screw guides and the like for targeting the precise location thereof, etc., as will now be apparent to those skilled in the art. The surgical site can then be closed and post-operative care can proceed in the normal manner now apparent to those skilled in the art.

Fourth, when it is desired to provide antegrade proximal locking of a left femur F as shown in FIGS. 47 and 48, a second intramedullary nail insert 63 is inserted into the cavity 25 in the proximal end 17 of the body 15 of the distally interlocked intramedullary nail 13. Because of the coaction between the flat 47 within the cavity 25 and the flat 94 on the body 81 of the intramedullary nail insert 63, proper alignment of the apertures 87, 89 through the intramedullary nail insert 63 and the transverse aperture 21 through the intramedullary nail 13 is insured. In addition to eliminating the possibility that the insert 63 could be placed incorrectly, the coaction of the flats 47, 94 keeps the insert 63 from rotating within the nail 13. The distal end 85 of the body 81 of the intramedullary nail insert 63 will rest or stop on the ledge 35 within the cavity 25 of the intramedullary nail 13. The ledge 35 thus acts as a force transmission member, transferring force from the insert 63 to the distal end 19 of the nail 13. Next, one of the intramedullary nail caps 111, 127, 145, 167, 183 is selected, depending upon the surgeon's discretion, and screwed into the proximal end 17 of the intramedullary nail 13 to secure the intramedullary nail insert 63 within the cavity 25 of the intramedullary nail 13. For example, the third intramedullary nail cap 145 is shown in FIG. 47, with the head portion 155 and undercut portion 157 of the cap 145 extending above the top or proximal end 17 of the nail 13 to be used to help extract the nail 13 from the femur F if extraction becomes desirable. More specifically, a removal instrument with a slap hammer attachment or the like having a hook or claw, etc., for hooking around the undercut portion 157 of the cap 145 or otherwise for engaging the head portion 155, can be used to extract the nail 13 as will now be apparent to those skilled in the art. The selected cap is merely screwed into the cavity 25 in the top of the nail 13, and the distal end of the selected cap contacts the top or proximal end 83 of the insert 63. The selected cap thus ensures contact between the insert 63 and the ledge 35 of the nail 13, and ensures that the insert 63 is completely seated and contacting the nail 13, and that the insert 63 cannot back out of or move within the nail 13. However, it should be noted that the selected insert and cap can, if desired, be inserted into and attached to the nail 13 together, as an integral unit, etc.

Next, at least one and preferably a spaced pair of proximal bone screws S are inserted at an angle through the lateral bone cortex of the femur F, through the aperture 21 in the proximal end 17 of the body 15 of the nail 13, through the apertures 87, 99 in the body 81 of the insert 63, and back out the medial cortex of the femur F as clearly shown in FIGS. 47 and 48. In the antegrade mode, the bone screws S travel down through the proximal femur F. Because of the built-in angled orientation of the apertures 87, 89 in the body 81 of the insert 63, the antegrade locking screws S are typically allowed to travel through the lesser trochanter LT of the femur F as clearly shown in FIG. 47 to increase bone purchase. The angled orientation of the central axes 93 of the apertures 87, 89 with respect to the plane of the flat 94 of the body 81 of the insert 63 also provides a degree of retroversion to the construct as clearly shown in FIG. 48. It should be noted that actual insertion of the proximal bone screws S can be performed in any typical manner using, for example, various proximal screw guides and the like for targeting the precise location thereof, etc., as will now be apparent to those skilled in the art. The surgical site can then be closed and post-operative care can proceed in the normal manner now apparent to those skilled in the art.

Fifth, when it is desired to provide reconstruction proximal locking of a left femur F to allow repair of femoral neck fractures as shown in FIGS. 49 and 50, a third intramedullary nail insert 65 is inserted into the cavity 25 in the proximal end 17 of the body 15 of the distally interlocked intramedullary nail 13. Because of the coaction between the flat 47 within the cavity 25 and the flat 108 on the body 95 of the intramedullary nail insert 65, proper alignment of the apertures 101, 103 through the intramedullary nail insert 65 and the transverse aperture 21 through the intramedullary nail 13 is insured. In addition to eliminating the possibility that the insert 65 could be placed incorrectly, the coaction of the flats 47, 108 keeps the insert 65 from rotating within the nail 13. The distal end 99 of the body 95 of the intramedullary nail insert 65 will rest or stop on the ledge 35 within the cavity 25 of the intramedullary nail 13. The ledge 35 thus acts as a force transmission member, transferring force from the insert 65 to the distal end 19 of the nail 13. Next, one of the intramedullary nail caps 111, 127, 145, 167, 183 is selected, depending upon the surgeon's discretion, and screwed into the proximal end 17 of the intramedullary nail 13 to secure the intramedullary nail insert 65 within the cavity 25 of the intramedullary nail 13. For example, a fourth intramedullary nail cap 167 is shown in FIG. 49, with the head portion 177 and undercut portion 179 of the cap 167 extending above the top or proximal end 17 of the nail 13 to be used to help extract the nail 13 from the femur F if extraction becomes desirable. More specifically, a removal instrument with a slap hammer attachment or the like having a hook or claw, etc., for hooking around the undercut portion 179 of the cap 167 or otherwise engaging the head portion 177, can be used to extract the nail 13 as will now be apparent to those skilled in the art. The selected cap is merely screwed into the cavity 25 in the top of the nail 13, and the distal end of the selected cap contacts the top or proximal end 97 of the insert 65. The selected cap thus ensures contact between the insert 65 and the ledge 35 of the nail 13, and ensures that the insert 65 is completely seated and contacting the nail 13, and that the insert 65 cannot back out of or move within the nail 13. However, it should be noted that the selected insert and cap can, if desired, be inserted into and attached to the nail 13 together, as an integral unit, etc.

Next, at least one and preferably a spaced pair of proximal bone screws S are inserted at an angle through the lateral bone cortex of the femur F, through the aperture 21 in the proximal end 17 of the body 15 of the nail 13, through the apertures 101, 103 in the body 95 of the insert 65, through the neck N of the femur F across any fracture or break B therein, and into the head H of the femur F as clearly shown in FIGS. 49 and 50. Thus, in this reconstruction mode, the bone screws S are placed through the nail 13 and insert 65, and travel through the femoral neck N and into the femoral head H. In order to stay centered within the femoral neck N (especially when using a reconstruction bone screw S having a length of 115 millimeters or so), the built-in angled orientation of the apertures 101, 103 in the body 95 of the insert 65, cause the reconstruction locking screws S to travel through the neck N of the femur F at an anatomical femoral neck angle of approximately 135° and an anteversion angle of approximately 12°. The angled orientation of the central axes 107 of the apertures 101, 103 with respect to the plane of the flat 108 of the body 95 of the insert 65 provides the degree of anteversion to the construct as clearly shown in FIG. 50, while the angled orientation of the central axes 107 of the apertures 101, 103 with respect to the central axis 105 of the body 95 of the insert 65 provides the anatomical femoral neck angle to the construct as clearly shown in FIG. 49. It should be noted that actual insertion of the proximal bone screws S can be performed in any typical manner using, for example, various proximal screw guides and the like for targeting the precise location thereof, etc., as will now be apparent to those skilled in the art. The surgical site can then be closed and post-operative care can proceed in the normal manner now apparent to those skilled in the art.

Sixth, when it is desired to provide active dynamic locking of a femur F as shown, for example, in FIG. 57, to allow repair of a fractured femoral shaft or the like, the intramedullary nail 13 is inserted into the intramedullary canal C and the distal end 19 thereof is locked to the femur F in the manner disclosed hereinabove. Next, the desired modified intramedullary nail insert having a deformable distal end portion or collar (e.g., the modified intramedullary nail insert 61 having the deformable distal end portion or collar 71') is inserted into the cavity 25 in the proximal end 17 of the body 15 of the distally interlocked intramedullary nail 13. Next, the selected intramedullary nail cap (e.g., the fifth intramedullary nail cap 183 as shown in FIG. 57) is screwed into the cavity 25 in the proximal end 17 of the body 15 of the distally interlocked intramedullary nail 13 on top of the insert. Next, at least one and preferably a spaced pair of bone screws S are then inserted either transversely as shown in FIG. 57, or at an angle, through the lateral bone cortex of the femur F, through the aperture 21 in the proximal end 17 of the body 15 of the nail 13, through the apertures in the body of the selected modified insert, and back out the medial cortex of the femur F. Once the bone screws S are thus loaded, the selected cap (e.g., the cap 183 as shown in FIG. 57) is further screwed into the cavity 25, thus further actively dynamically compressing the fracture and causing the deformable end portion or collar of the selected insert (e.g., the deformable end portion or collar 71' of the insert 61 as shown in FIG. 57) to collapse, allowing the distance between the proximal and distal bone screws to compress and stabilize the fracture fragments. It should be noted that not all fracture patterns are stable enough to be actively compressed.

As thus constructed and used, the present invention provides a modular intramedullary fixation system which eliminates the need for unique right and left intramedullary nails. Additionally, the modularity allows multiple configurations of proximal locking including transverse (with static, dynamic or active dynamic compression), antegrade (with static or active dynamic compression), and reconstruction (with static or active dynamic compression). Modularity is achieved by the proximal geometry of the nail 13 and the specific inserts 61, 63, 65, etc., that fit inside the proximal nail 13. All locking modes accommodate two parallel proximal screws S simultaneously. The slot-shaped specific design of the transverse aperture 21 through the proximal end 17 of the body 15 of the nail 13 (e.g., the generally stylized S-shape cross section shown generally in FIG. 3 or the relative large oval shape cross section shape as shown generally in FIG. 52) allows one or more proximal bone screw S to be inserted through the transverse aperture 21 and through the proximal end 17 of the body 15 with the longitudinal axis of the proximal bone screws S located at an angle to the central axis 23 of the body 15 of the nail 13 within a range between an acute angle on either side of a plane extending transverse to the central axis 23 of the body of the nail 13, including a right or transverse angle to the central axis 23 of the body 15 of the nail 13 as shown in FIGS. 39, 41 and 57, an acute angle on the proximal side of a plane extending at right or transverse angle to the central axis 23 of the body 15 of the nail 13 as shown in FIGS. 43 and 49, and an acute angle on the distal side of the plane extending at right or transverse angle to the central axis 23 of the body 15 of the nail 13 as shown in FIGS. 45 and 49. The proximal nail 13 is able to accommodate all of these locking modes and inserts as rights and lefts due to the slot-shaped specific design of the transverse aperture 21. The slot-shaped specific design of the transverse aperture 21 also allows anteversion and retroversion, which is used in the reconstruction and antegrade modes respectively, and its symmetry allows rights and lefts with the same nail 13. The slot-shaped specific design of the transverse aperture 21 also allows static, dynamic and active dynamic compression modes in conjunction with transverse locking, and allows static and active dynamic compression modes in conjunction with antegrade and reconstruction locking. Because the proximal nail 13 is asymmetrical to reduce the chance of placing the inserts 61, 63, 65, etc., incorrectly, two inserts 63, 65, etc., are required for left and right antegrade and reconstruction options. Reconstruction left positions the insert in the same position as antegrade right, and reconstruction right is identical to antegrade left positioning. The asymmetry in the proximal nail 13 is caused by flats 45, 47 that are formed into the inner and outer diameters of the proximal section of the nail 13. In static locking of the intramedullary nail 13 (see, in general, FIGS. 39), the bone screws S hold the fracture fragments at length without allowing controlled collapse. In dynamic locking of the intramedullary nail 13 (see, in general, FIG. 41), controlled collapse of the fracture is allowed by the bone screws S sliding in transverse slots or apertures. In active dynamic compression, after the fracture is transfixed, and the fracture site is actively compressed through the selected intramedullary nail cap, the deformable portion or collar 76' allows up to 10 millimeters or so of active screw compression. Further, because of the relative large ports in the nail 13 formed by the openings 26 of the transverse aperture 21 through the proximal end 17 of the body 15 of the nail 13, substantial quantities of bone graft and/or cement can be delivered by a syringe or the like through the cavity 25 in the body 15 of the nail 13 and through the openings 26 to areas of the intramedullary canal C of the femur F adjacent the openings 26 after the nail 13 has been inserted in the intramedullary canal C but before the selected insert and cap has been loaded into the cavity 25. Such an option is highly advantageous in cases of severe osteopenia or tumor when fixation of a fracture needs to be supplemented by bone graft or cement, etc.

Preferred embodiments of the insertion instrumentation of the present invention are shown in FIGS. 58–76. The insertion instrumentation of the present invention is especially designed for use with the modular intramedullary fixation system of the present invention for intramedullary fixation and reconstruction of femoral fractures and the like.

The insertion instrumentation of the present invention preferably includes intramedullary nail insert and cap inserter instrumentation 201 for use in inserting one of the intramedullary nail inserts 61, 63, 65, etc., and one of the intramedullary nail caps 111, 127, 145, 167, 183, etc., into the cavity 25 in the proximal end 17 of the body 15 of the intramedullary nail 13. In general, the intramedullary nail insert and cap inserter instrumentation 201 is a two piece instrument including two coaxial shafts, an inner shaft for being attached to one of the intramedullary nail inserts 61, 63, 65, etc., so that rotation of in inner shaft will cause the attached intramedullary nail inserts 61, 63, 65, etc., to likewise rotate; and an outer shaft for being attached to one of the intramedullary nail caps 111, 127, 145, 167, 183, etc., so that rotation of the outer shaft will cause the attached intramedullary nail caps 111, 127, 145, 167, 183, etc., to likewise rotate.

Figure 58:
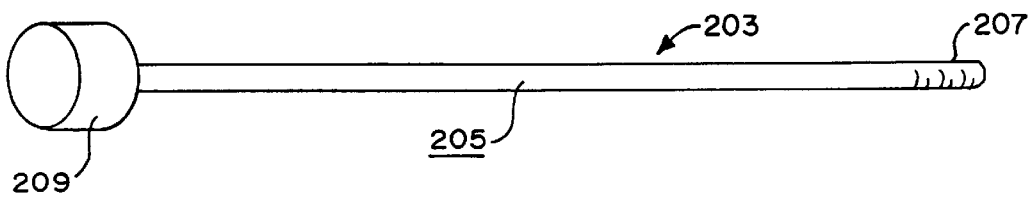
FIG. 58 is a perspective view of a first embodiment of an inner member of an intramedullary nail insert and cap inserter instrumentation of the present invention.
Figure 61:
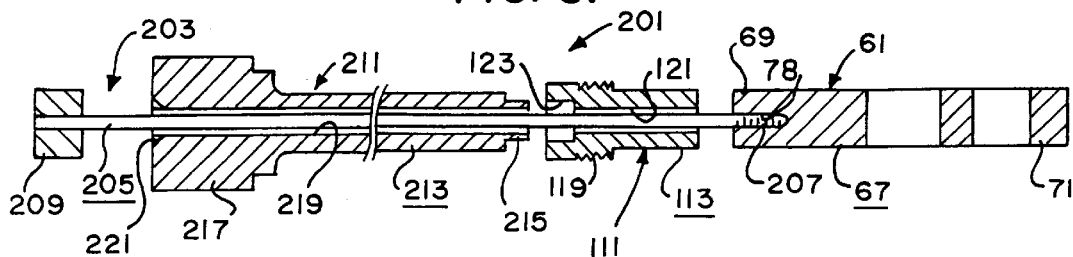
FIG. 61 is a somewhat diagrammatic sectional view of the inner and outer members of FIGS. 58 and 59, shown combined with the first intramedullary nail insert of FIGS. 5–9 and the first intramedullary nail cap of FIGS. 20–23.

A first embodiment of the inner shaft is shown in FIGS. 58 and 61, and identified by the numeral 203. The inner shaft 203 includes a solid, rigid body 205 having a first end 207 adapted to be attached to a selected one of the intramedullary nail inserts 61, 63, 65, etc., and a second end 209 adapted to be easily rotated by a surgeon, etc. For example, the first end 207 preferably includes an externally threaded portion for being screwed into the internally threaded bore in the proximal end of a selected one of the intramedullary nail inserts 61, 63, 65, etc. The second end 209 is preferably adapted to be easily rotated by a surgeon, etc. For example, the second end 209 may have an enlarged head or the like to provide the surgeon with a good grip thereon, etc.

Figure 59:
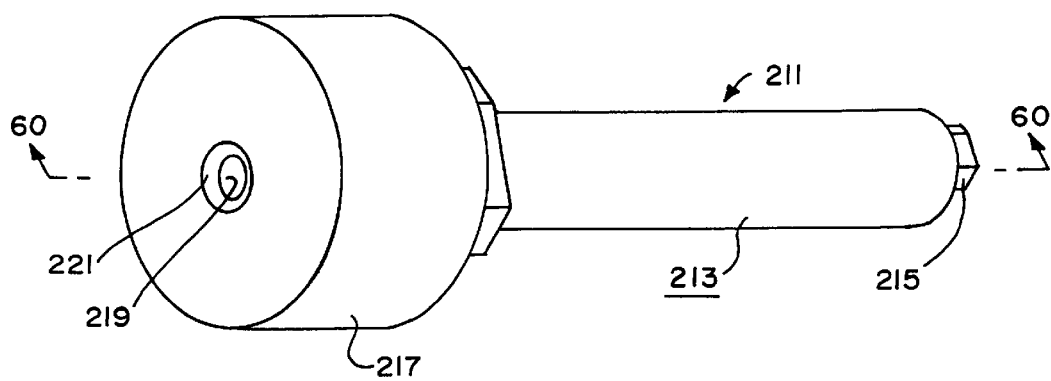
FIG. 59 is a perspective view of a first embodiment of an outer member of the intramedullary nail insert and cap insert instrumentation of the present invention.
Figure 60:
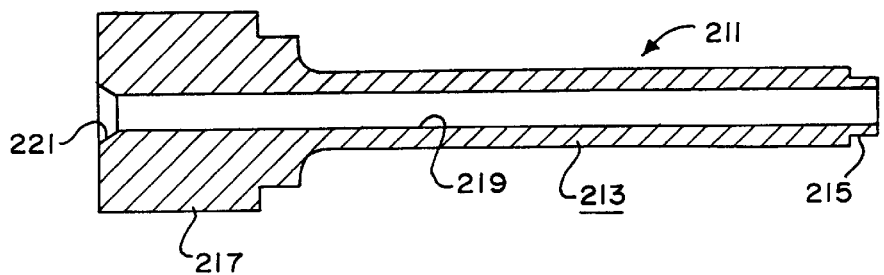
FIG. 60 is a sectional view substantially as taken on line 60—60 of FIG. 59.

A first embodiment of the outer shaft is shown in FIGS. 59–61 and identified by the numeral 211. The outer shaft 211 includes a rigid body 213 having a first end 215 adapted to drivably engage the hexagonal socket, etc., of a selected one of the intramedullary nail caps 111, 127, 145, 167, 183, etc., and having a second end 217 adapted to be easily rotated by a surgeon, etc. For example, the first end 215 may have a distal end with a hexagonal cross sectional shape or the like for providing a hex drive to engage the hexagonal socket, etc., of a selected one of the intramedullary nail caps 111, 127, 145, 167, 183, etc. The second end 217 may have a hex drive to allow a wrench or the like to be used thereon to rotate the body 213, or may have an enlarged head with a knurled outer surface, etc., to provide the surgeon with a good grip thereon, etc. In addition, the body 213 has an aperture 219 extending completely therethrough, sized to allow the first end 207 of the body 205 of the inner shaft 203 to extend therethrough. The distal end of the aperture 219 at the second end 217 of the body 213 is preferably bevelled to aid the insertion of the first end 207 of the body 205 of the inner shaft 203 therethrough.

As illustrated diagrammatically in FIG. 61, to use the inserter instrumentation 201 with, for example, the intramedullary nail insert 61 and the intramedullary nail cap 111, the first end 207 of the body 205 of the inner shaft 203 is first inserted through the aperture 219 in the body 213 of the outer shaft 211, then inserted through the aperture 121 through the body 113 of the intramedullary nail cap 111, and then screwed into the internally threaded bore 78 in the proximal end 69 of the body 67 of the intramedullary nail insert 61. The construct or assembly can then be moved and handled as a single unit. For example, to insert the nail insert 61 and nail cap 111 into the opened mouth 37 of the cavity 25 in the proximal end 17 of the body 15 of the intramedullary nail 13 using the construct or assembly shown in FIG. 61, the distal end 71 of the body 67 of the insert 61 is merely inserted into the opened mouth 37 of the cavity 25, using the inserter instrumentation 201 as a handle, etc. The surgeon can then rotate the inner shaft 203 by turning the second end 209 of the body 205 to properly orient the body 67 of the nail insert 61 with the cavity 25, and then fully insert the nail insert 61 into the cavity 25. Next, the surgeon can slide the nail cap 111 and outer shaft 211 along the inner shaft 203 until the externally threaded portion 119 of the nail cap 111 engages the internally threaded portion 39 of mouth 37 of the cavity 25, and the second end 217 of the body 213 of the outer shaft 211 operatively engages the hexagonal shaped socket 123 of the nail cap 111. The surgeon can then rotate the outer shaft 211 to screw the nail cap 111 into the cavity 25 and thereby secure the nail cap 111 and nail insert 61 to the nail 13 in the proper locations. The outer shaft 211 can then be slid back to disengage from the nail cap 111. The inner shaft 203 will then be rotated to unscrew from the insert 61. The inserter instrumentation 201 can then be completely removed.

Figure 62:
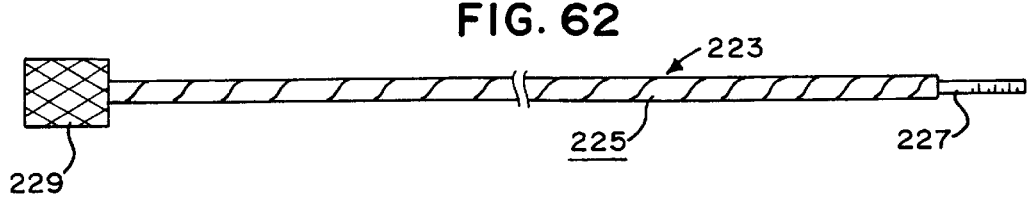
FIG. 62 is an elevational view of a second embodiment of an inner member of a the intramedullary nail insert and cap inserter instrumentation of the present invention.

A second embodiment of the inner shaft is shown in FIG. 62, and identified by the numeral 223. The inner shaft 223 includes a flexible body 225 having a first end 227 adapted to be attached to a selected one of the intramedullary nail inserts 61, 63, 65, etc., and a second end 229 adapted to be easily rotated by a surgeon, etc. For example, the first end 227 preferably includes a rigid externally threaded portion for being screwed into the internally threaded bore in the proximal end of a selected one of the intramedullary nail inserts 61, 63, 65, etc. The second end 229 may be enlarged or otherwise adapted to be easily rotated by a surgeon, etc. For example, the outer surface of the second end 229 may be knurled to provide the surgeon with a good grip thereon, etc.

Figure 63:
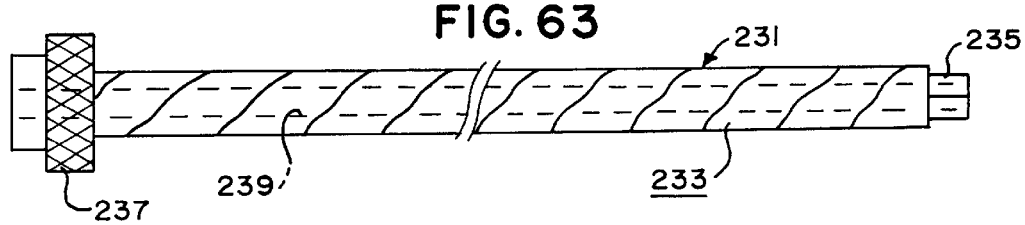
FIG. 63 is an elevational view of a second embodiment of an outer member of the intramedullary nail insert and cap insert instrumentation of the present invention.

A second embodiment of the outer shaft is shown in FIG. 63 and identified by the numeral 231. The outer shaft 231 includes a flexible body 233 having a first end 235 adapted to drivably engage the hexagonal socket, etc., of a selected one of the intramedullary nail caps 111, 127, 145, 167, 183, etc., and having a second end 237 adapted to be easily rotated by a surgeon, etc. For example, the first end 235 may have a rigid distal end with a hexagonal cross sectional shape or the like for providing a hex drive to engage the hexagonal socket, etc., of a selected one of the intramedullary nail caps 111, 127, 145, 167, 183, etc. The second end 237 may have an enlarged head with a knurled outer surface, etc., to provide the surgeon with a good grip thereon, etc. In addition, the body 233 has an aperture 239 extending completely therethrough, sized to allow the first end 227 of the body 225 of the inner shaft 223 to extend therethrough.

Figure 64:
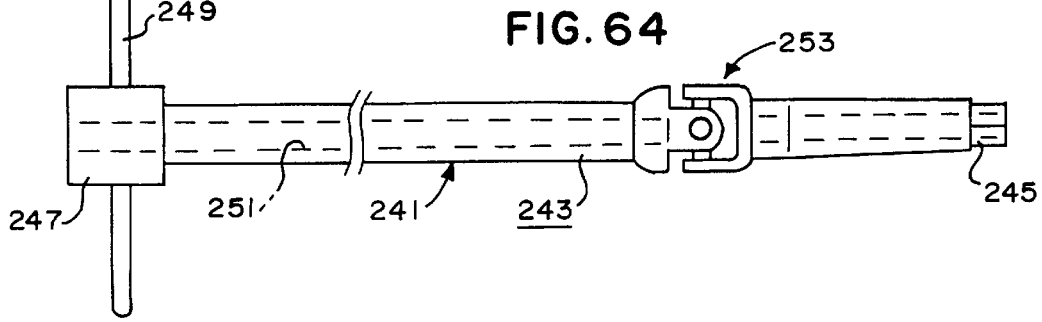
FIG. 64 is an elevational view of a third embodiment of an outer member of the intramedullary nail insert and cap insert instrumentation of the present invention.
Figure 68:
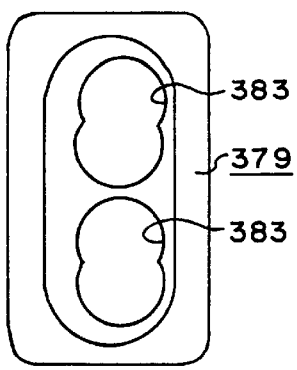
FIG. 68 is a left end elevational view of a cross screw guide for use with the intramedullary nail insertion handle instrumentation of FIG. 65.
Figure 69:
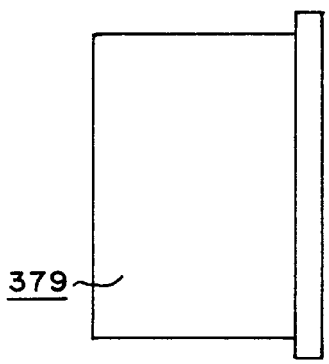
FIG. 69 is a side elevational view of the cross screw guide of FIG. 68.
Figure 70:
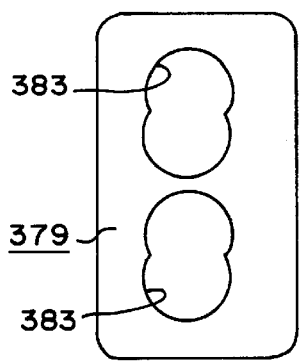
FIG. 70 is a right end elevational view of the cross screw guide of FIG. 68.
Figure 71:
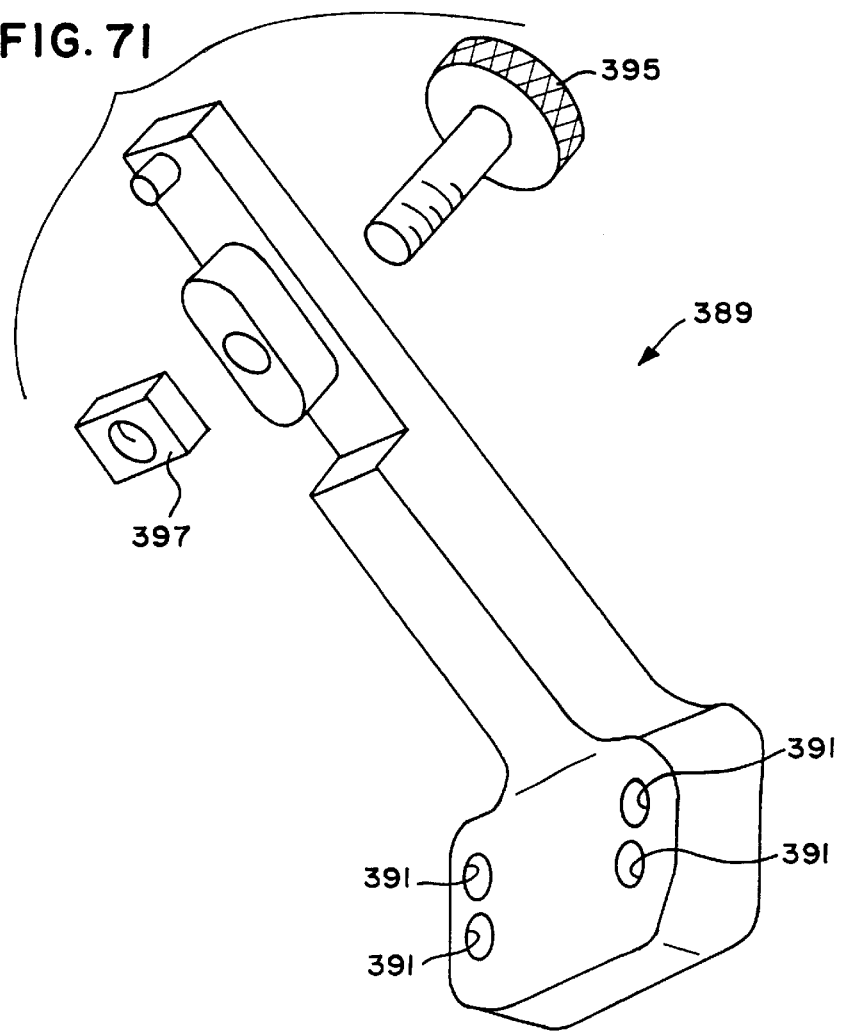
FIG. 71 is an exploded perspective view of a reconstruction screw guide assembly for use with the intramedullary nail insertion handle instrumentation of FIG. 65.

A third embodiment of the outer shaft is shown in FIG. 64 and identified by the numeral 241. The outer shaft 241 includes a body 243 having a first end 245 adapted to drivably engage the hexagonal socket, etc., of a selected one of the intramedullary nail caps 111, 127, 145, 167, 183, etc., and having a second end 247 adapted to be easily rotated by a surgeon, etc. For example, the first end 245 may have a distal end with a hexagonal cross sectional shape or the like for providing a hex drive to engage the hexagonal socket, etc., of a selected one of the intramedullary nail caps 111, 127, 145, 167, 183, etc. The second end 247 may include a transverse bar 249 to form a T-handle or the like that provides the surgeon with a positive grip thereon, etc. In addition, the body 243 has an aperture 251 extending completely therethrough, sized to allow the first end 227 of the body 225 of the inner shaft 223 to extend therethrough. In addition, the body 243 preferably has a universal joint 253 between the first and second ends 245, 247 thereof.

The combination of a flexible inner shaft and a flexible outer shaft (either a flexible shaft per se or a shaft having a universal joint) allows the inserter instrumentation to bend to work with varying exposure, incision location and size, etc. The two-piece rigid outer shaft joined by a universal joint also provides maximum torque control for tightening the selected cap into place, etc.

The insertion instrumentation of the present invention preferably includes intramedullary nail insertion handle instrumentation 301 (see, in general, FIGS. 65–76) that provides a surgical instrument for use during insertion intramedullary nail insertion.

The insertion handle instrumentation 301 includes a body 303 having a first end 305 adapted to be attached to the proximal end of an intramedullary nail, especially the proximal end 17 of the intramedullary nail 13, and a second end 307 adapted to be located outside the proximal incision PI made to provide surgical access to the proximal end of the femur F, to allow easy position and manipulation of the nail 13 during insertion, etc.

Figure 72:
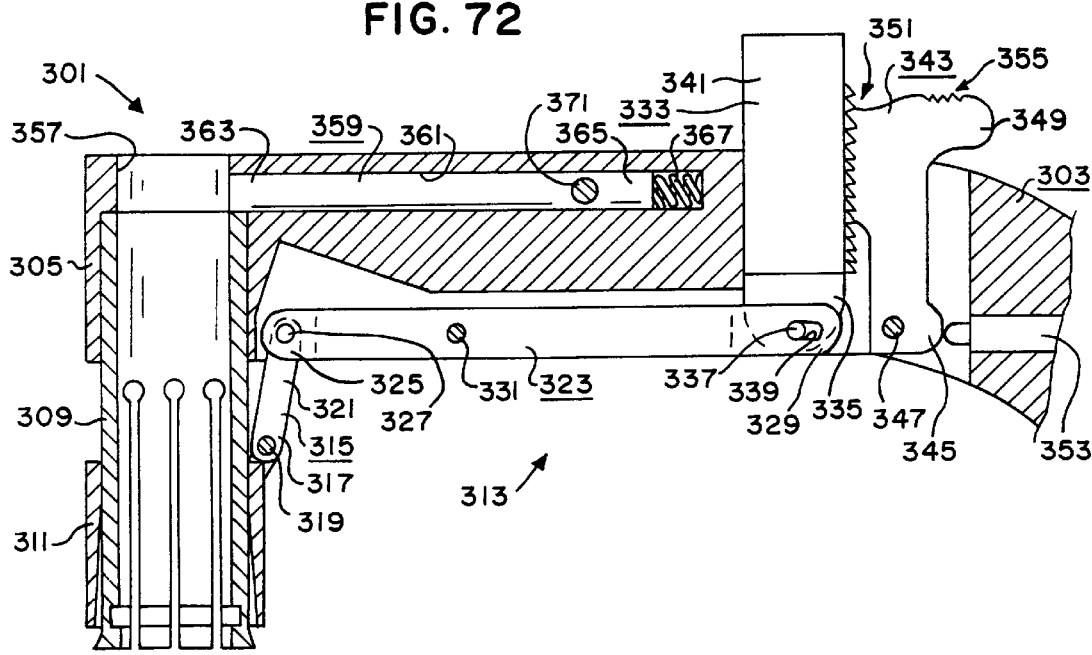
FIG. 72 is a somewhat diagrammatic sectional view of a portion of the intramedullary nail insertion handle instrumentation of FIG. 65.
Figure 73:
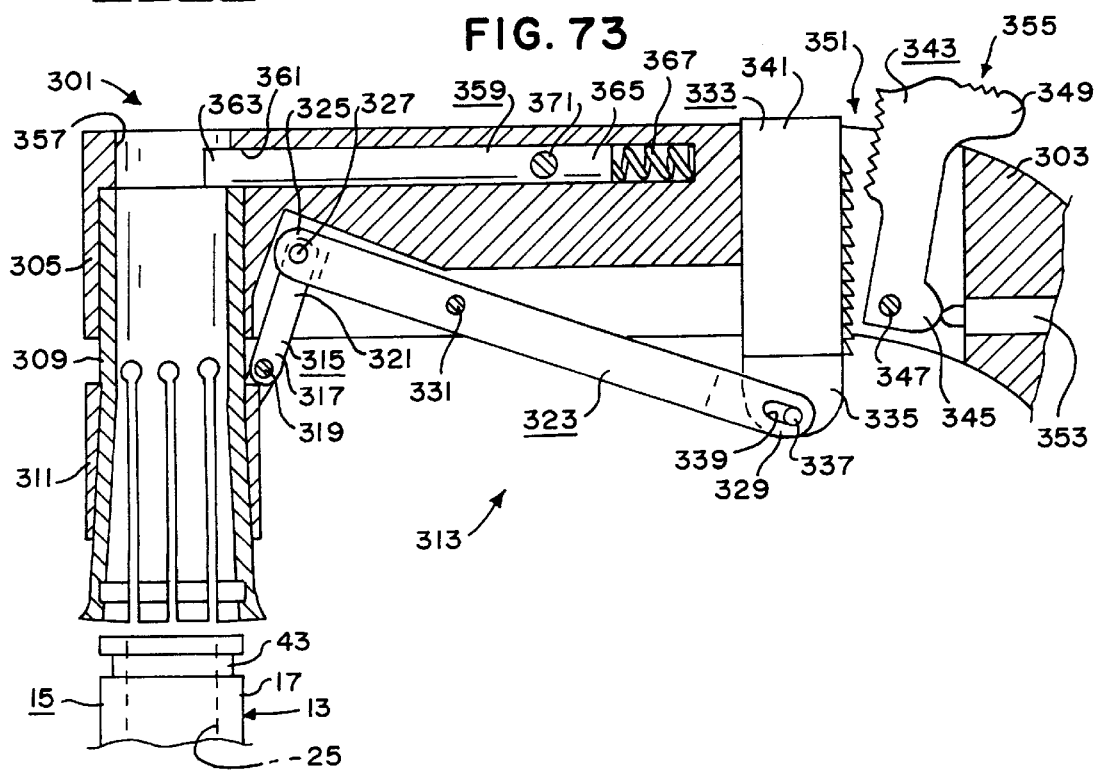
FIG. 73 is a somewhat diagrammatic sectional view similar to FIG. 72 but showing certain components thereof in a moved position.
Figure 74:
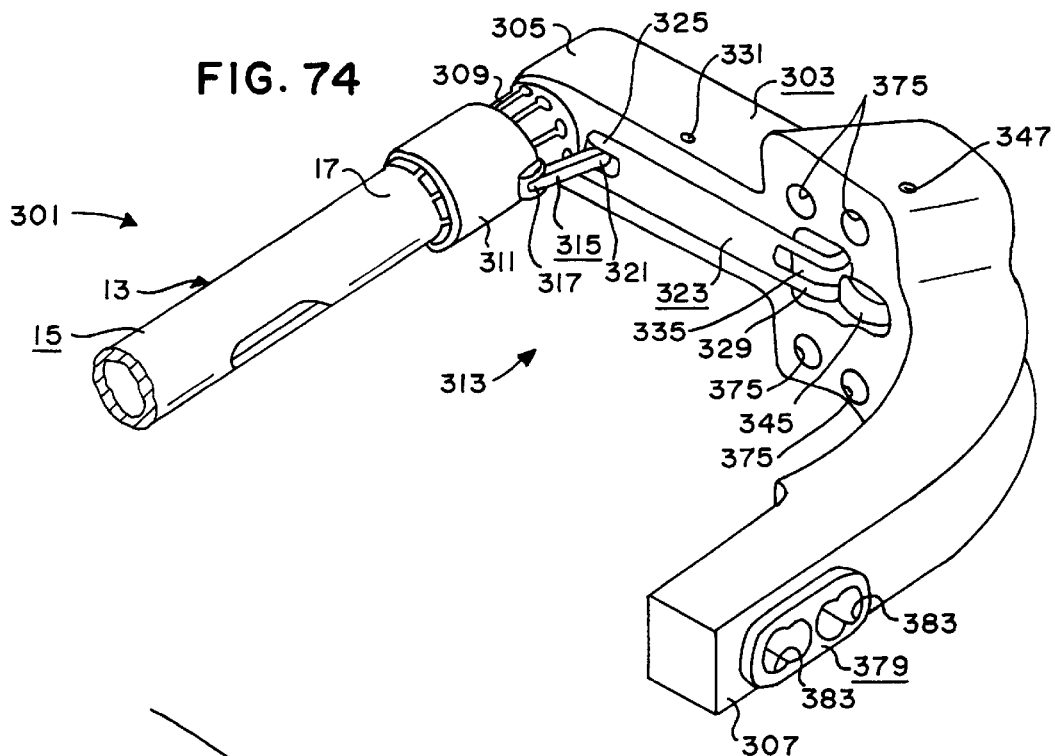
FIG. 74 is a perspective view of the intramedullary nail insertion handle instrumentation of FIG. 65, shown attached to the proximal end of an intramedullary nail.
Figure 75:
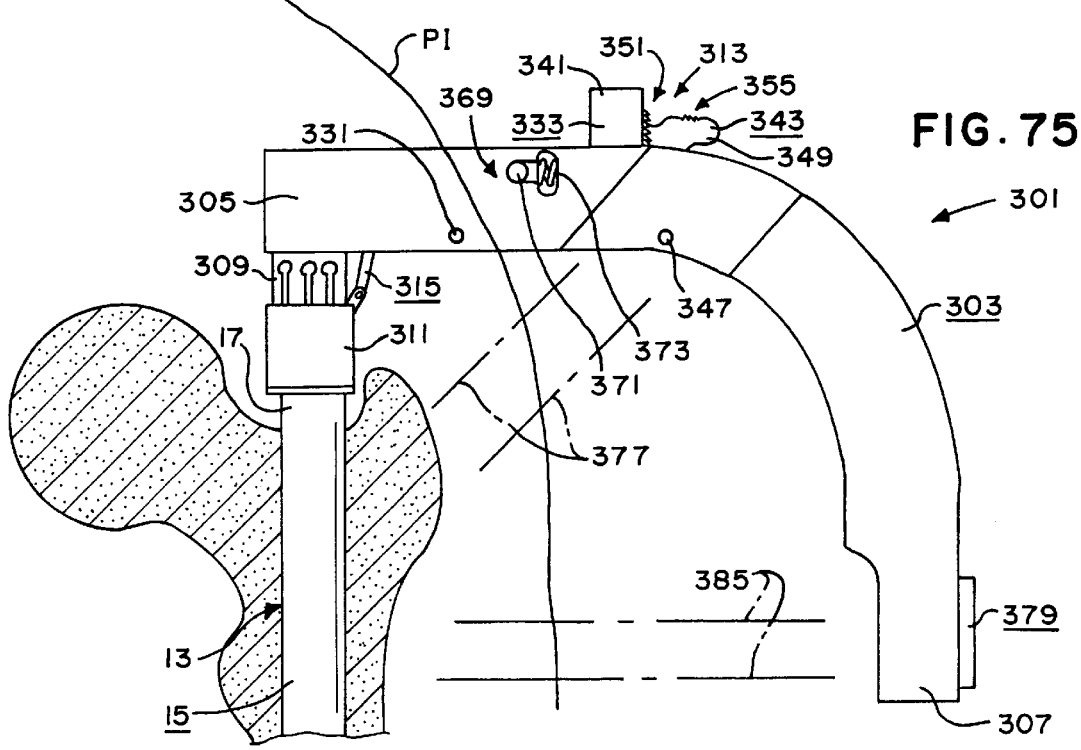
FIG. 75 is a somewhat diagrammatic elevational view of the intramedullary nail insertion handle instrumentation and intramedullary nail assembly of FIG. 74 combined with the cross screw guide of FIGS. 68–70 and with a human femur, with the instrumentation configured for guiding proximal locking screw in either transverse or antegrade modes.

The insertion handle instrumentation 301 includes a collet 309 or the like mounted at the first end 305 of the body 303 for attachment to the proximal end 17 of the nail 13, etc. The collet 309 includes spring-type fingers that are normally urged to an opened position (see FIG. 73) that allow the collet 309 to be easily placed over and removed from the distal end 17 of the nail 13. The insertion handle instrumentation 301 includes a collet sleeve 311 mounted over the collet 309 for movement between a first position as shown in FIG. 72 in which the fingers of the collet 309 are forced closed and a second position as shown in FIG. 73 in which the fingers of the collet 309 are allowed to spring open. The inner side of each of the spring-type fingers of the collet 309 preferably has a transverse groove that, in effect, forms an inwardly projecting lip on the extreme distal end of each of the spring-type fingers to engage the transverse groove 43 in the outer surface 41 at the proximal end 17 of the nail 13 to greatly increase the clamping power of the collet 309 with combined with such a nail 13.

The insertion handle instrumentation 301 includes control means 313 for allowing the user thereof to cause the collet sleeve 311 to move between the first and second positions. The control means 313 preferably includes a collet sleeve link arm 315 having a first end 317 pivotally attached to the collet sleeve 311 via a pivot rod 319, and having a second end 321. The control means 313 preferably includes a button beam 323 having a first end 325 pivotally attached to the second end 321 of the collet sleeve link arm 315 via a pivot rod 327, and having a second end 329. The button beam 323 is pivotally attached to the body 303 via a pivot rod 331 at a pivot point intermediate the first and second ends 325, 329 thereof. The control means 313 preferably includes a control button 333 having a first end 335 pivotally attached to the second end 329 of the button beam 323 via a pivot rod 337 and an elongated slot 339, and having a second end 341. The control means 313 preferably includes a button latch 343 for coacting with the control button 333 to lock the collet sleeve 311 in the first or second position. The button latch 343 preferably has a first end 345 pivotally attached to the body 303 via a pivot rod 347, and has a second end 349. The control button 333 and button latch 343 preferably have coacting teeth 351 to selectively and securely hold one another in position as will hereinafter become apparent. The control means 313 may include urging means 353 such as a typical button plunger or the like, to normally urge the button latch 343 against the control button 333. The control button 333 and button latch 343 are mounted to the body 303 in such a manner that the second ends 341,349 thereof are located outside the proximal incision PI even after the nail 13 has been fully inserted into the intramedullary canal C of the femur F. and can be easily manipulated by the surgeon to release the nail 13 from the insertion handle instrumentation 301. More specifically, as will be apparent to those skilled in the art from the drawings, the collet sleeve 311 will move from the first or locked position as shown in FIG. 72 to the second or unlocked position as shown in FIG. 73 when the control button 333 is manually pressed downward (as viewed in FIGS. 72 and 73) from the position as shown in FIG. 72 to the position as shown in FIG. 73, allowing the insertion handle instrumentation 301 to be easily removed from (or inserted over) the proximal end 17 of the body 15 of the nail 13. To easily press the control button 33 downward, the button latch 343 should be rotated clockwise as viewed in FIGS. 72 and 73, to the position shown in FIG. 73. The second end 349 of the button latch 343 may have a knurled portion 355 or the like to provide the surgeon with a good grip thereon, etc.

The first end 305 of the body 303 preferably has an aperture 357 therethrough that receives the proximal end of the collet 309 and that coacts with the interior of the collet 309 to provide a continuous opening that is coextensive with the cavity 25 of the nail 13 when the nail 13 is attached to the insertion handle instrumentation 301. The continuous opening through the insertion handle instrumentation 301 is preferably sized so that it is at least as large, or larger, than the diameter of the cavity 25 of the nail 13, and does not obstruct any portion of the cavity 25 of the nail 13, thereby allowing items, such as slap hammers, distal locking positioners, inserts, caps, etc., to be freely fed down into the cavity 25 of the nail 13.

The insertion handle instrumentation 301 may include an impactor plunger 359 slidably mounted within an aperture 361 in the body 303, and having a first end 363 for selectively extending into the aperture 357 to lock various items such as slap hammers, distal locking positioners, etc., to the insertion handle instrumentation 301, and having a second end 365. A coil spring 367 is preferably positioned within the aperture 361 at the second end 365 of the impactor plunger 359 to normally urge the first end 363 of the impactor plunger 359 into the aperture 357 as shown in FIG. 73. Lock means 369 is preferably provided to selectively move and lock the impactor plunger 359 in the retracted position as shown in FIG. 72. The lock means 369 may consist simply of a cross bar 371 extending through the impactor plunger 359 and T-shaped apertures 373 in the body 303 for allowing the cross bar 371 to extend therethrough. Manual movement of the cross bar 371 in the T-shaped apertures 373 allows the surgeon to selectively move the impactor plunger 359 to the retracted position, and rotation of the cross bar 371 into the end of the T-shaped apertures 373 will lock the impactor plunger 359 in that retracted position as will now be apparent to those skilled in the art. The cross bar 371 and T-shaped apertures 373 are preferably located on the body 303 in a position so that the cross bar 371 can be easily manipulated by the surgeon outside the proximal incision PI even after the nail 13 has been fully inserted into the intramedullary canal C of the femur F.

The body 303 preferably includes antegrade guide bores 375 positioned so as to guide the insertion of proximal locking screws along antegrade axes 377 (see FIG. 75) in the antegrade locking mode for either a right or left femur.

The insertion handle instrumentation 303 preferably includes a cross or transverse guide insert 379 for being positioned in a slot 381 in the body 303, and having cross or transverse guide bores 383 positioned so as to guide the insertion of proximal locking screws along transverse axes 385 (see FIG. 75) in both static and dynamic modes as explained hereinabove. A ball plunger 387 or the like is preferably provided in the body 303 to secure the insert 379 to the body 303.

The insertion handle instrumentation 303 preferably includes a reconstruction guide assembly 389 for being attached to the body 303, and having reconstruction guide bores 391 positioned so as to guide the insertion of proximal locking screws along reconstruction axes 393 (see FIG. 76). The reconstruction guide assembly 389 preferably includes a screw 395 and a nut 397 for use in securing the reconstruction guide assembly 389 to the body 303.

Portions of the insertion handle instrumentation 301 may be made from a radiolucent material so as not to interfere with x-ray images during nail insertion.

Although the present invention has been described and illustrated with respect to a preferred embodiment and a preferred use therefor, it is not to be so limited since modifications and changes can be made therein which are within the full intended scope of the invention.

We claim:

1. A modular intramedullary fixation system comprising:
    (a) an intramedullary nail including an elongated body having a proximal end and a distal end; the proximal end of the body of the intramedullary nail having a transverse aperture therethrough; the body of the intramedullary nail having a central axis extending between the proximal and distal ends thereof, the proximal end of the body of the intramedullary nail having a cavity extending along the central axis thereof toward the distal end thereof and having a protuberance within the cavity thereof at a location adjacent the transverse aperture, and
    (b) an intramedullary nail insert for insertion into the cavity of the proximal end of the body of the intramedullary nail, the intramedullary nail insert including an elongated body having a proximal end and a distal end; the body of the intramedullary nail insert having a transverse aperture therethrough for alignment with the transverse aperture through the proximal end of the body of the intramedullary nail when the intramedullary nail insert is inserted in to the cavity of the proximal end of the body of the intramedullary nail with the distal end of the body of the intramedullary nail insert engaging the protuberance within the cavity of the proximal end of the body of the intramedullary nail so that force is transferred between the intramedullary nail insert and intramedullary nail.

2. The modular intramedullary fixation system of claim 1 in which the body of the intramedullary nail insert has a second transverse aperture therethrough for alignment with the transverse aperture through the proximal end of the body of the intramedullary nail when the intramedullary nail insert is inserted into the cavity of the proximal end of the body of the intramedullary nail; each of the transverse apertures through the intramedullary nail insert having a central axis.

3. The modular intramedullary fixation system of claim 1 in which is included means for insuring alignment of the transverse aperture through the body of the intramedullary nail insert with the transverse aperture through the proximal end of the body of the intramedullary nail when the intramedullary nail insert is inserted into the cavity of the proximal end of the body of the intramedullary nail.

4. The modular intramedullary fixation system of claim 1 in which the cavity of the proximal end of the body of the intramedullary nail has contour with a non-circular cross section; and in which the body of the intramedullary nail insert has a contour with a non-circular cross section that substantially corresponds to the shape of the contour of the cavity of the proximal end of the body of the intramedullary nail to insure alignment of the transverse aperture through the body of the intramedullary nail insert with the transverse aperture through the proximal end of the body of the intramedullary nail when the intramedullary nail insert is inserted into the cavity of the proximal end of the body of the intramedullary nail.

5. A modular intramedullary fixation system comprising:
    (a) an intramedullary nail including an elongated body having a proximal end and a distal end; the proximal end of the body of the intramedullary nail having a transverse aperture therethrough; the body of the intramedullary nail having a central axis extending between the proximal and distal ends thereof; the proximal end of the body of the intramedullary nail having a cavity extending along the central axis thereof toward the distal end thereof; and
    (a) an intramedullary nail insert for insertion into the cavity of the proximal end of the body of the intramedullary nail, the intramedullary nail insert including an elongated body having a proximal end and distal end, the body of the intramedullary nail insert having a transverse aperture therethrough for alignment with the transverse aperture through the proximal end of the body of the intramedullary nail when the intramedullary nail insert is inserted into the cavity of the proximal end of the body of the intramedullary nail, the body of the intramedullary nail insert having a second transverse aperture therethrough for alignment with the transverse aperture through the proximal end of the body of the intramedullary nail when the intramedullary nail insert is inserted in to the cavity of the proximal end of the body of the intramedullary nail, each of the transverse apertures through the intramedullary nail insert having a central axis; the central axes of each of the transverse apertures through the intramedullary nail insert are parallel to one another and perpendicular to the central axis of the body of the intramedullary nail insert.

6. A modular intramedullary fixation system comprising:
    (a) an intramedullary nail including an elongated body having a proximal end and a distal end; the proximal end of the body of the intramedullary nail having a transverse aperture therethrough; the body of the intramedullary nail having a central axis extending between the proximal and distal ends thereof, the proximal end of the body of the intramedullary nail having a cavity extending along the central axis thereof toward the distal end thereof; and
    (b) an intramedullary nail insert for insertion into the cavity of the proximal end of the body of the intramedullary nail the intramedullary nail insert including an elongated body having a proximal end and a distal end; the body of the intramedullary nail insert having a transverse aperture therethrough for alignment with the transverse aperture through the proximal end of the body of the intramedullary nail when the intramedullary nail insert is inserted into the cavity of the proximal end of the body of the intramedullary nail; the body of the intramedullary nail insert having a second transverse aperture therethrough for alignment with the transverse aperture through the proximal end of the body of the intramedullary nail when the intramedullary nail insert is inserted in to the cavity of the proximal end of the body of the intramedullary nail; each of the transverse apertures through the intramedullary nail insert having a central axis; the central axes of each of the transverse apertures through the intramedullary nail insert are parallel to one another and angled relative to the central axis of the body of the intramedullary nail.

7. A modular intramedullary fixation system comprising:
(a) an intramedullary nail including an elongated body having a proximal end and a distal end, the proximal end of the body of the intramedullary nail having a transverse aperture therethrough; the body of the intramedullary nail having a central axis extending between the proximal and distal ends thereof; the proximal end of the body of the intramedullary nail having a cavity extending along the central axis thereof toward the distal end thereof; the transverse aperture through the proximal end of the body of the intramedullary nail having contour with an S-shape cross section; and
(b) an intramedullary nail insert for insertion into the cavity of the proximal end of the body of the intramedullary nail, the intramedullary nail insert including an elongated body having a proximal end and a distal end; the body of the intramedullary nail insert having a transverse aperture therethrough for alignment with the transverse aperture through the proximal end of the body of the intramedullary nail when the intramedullary nail insert in inserted into the cavity of the proximal end of the body of the intramedullary nail.

8. A modular intramedullary fixation system comprising:
(a) an intramedullary nail including an elongated body having a proximal end and a distal end; the proximal end of the body of the intramedullary nail having a transverse aperture therethrough; the body of the intramedullary nail having a central axis extending between the proximal and distal ends thereof; the proximal end of the body of the intramedullary nail having a cavity extending along the central axis thereof toward the distal ends thereof, the cavity of the proximal end of the body of the intramedullary nail having a contour with a non-circular cross section; and
(b) an intramedullary nail insert for insertion into the cavity of the proximal end of the body of the intramedullary nail, the intramedullary nail insert including an elongated body having a proximal end and a distal end; the body of the intramedullary nail insert having a transverse aperture therethrough for alignment with the transverse aperture through the proximal end of the body of the intramedullary nail when the intramedullary nail insert is inserted into the cavity of the proximal end of the body of the intramedullary nail; the body of the intramedullary nail insert having a contour with a non-circular cross section that substantially corresponds to the shape of the contour of the cavity of the proximal end of the body of the intramedullary nail to insure alignment of the transverse aperture through the body of the intramedullary nail insert with the transverse aperture through the proximal end of the body of the intramedullary nail when the intramedullary nail insert is inserted into the cavity of the proximal end of the body of the intramedullary nail.

9. The modular intramedullary fixation system of claim 8 in which the intramedullary nail cap has a flush top for positioning flush with the proximal end of the intramedullary nail when fixing the intramedullary nail insert within the cavity of the proximal end of the body of the intramedullary nail.

10. The modular intramedullary fixation system of claim 8 in which the intramedullary nail cap has an extended top for extending above the proximal end of the intramedullary nail when fixing the intramedullary nail insert within the cavity of the proximal end of the body of the intramedullary nail.

11. A modular intramedullary fixation system comprising:
(a) an intramedullary nail including an elongated body having a proximal end and a distal end; the proximal end of the body of the intramedullary nail having a transverse aperture therethrough; the body of the intramedullary nail having a central axis extending between the proximal and distal ends thereof, the proximal end of the body of the intramedullary nail having a cavity extending along the central axis thereof toward the distal end thereof, and
(b) an intramedullary nail insert for insertion into the cavity of the proximal end of the body of the intramedullary nail, the intramedullary nail insert including an elongated body having a proximal end and a distal end; the body of the intramedullary nail insert having a transverse aperture therethrough for alignment with the transverse aperture through the proximal end of the body of the intramedullary nail when the intramedullary nail insert is inserted into the cavity of the proximal end of the body of the intramedullary nail; the intramedullary nail insert having a deformable portion for allowing active dynamic intramedullary fixation.

12. In combination, a modular intramedullary fixation system and a magnetic positioner instrumentation including a target magnet; the modular intramedullary fixation system comprising:
(a) an intramedullary nail including an elongated body having a proximal end and a distal end; the body of the intramedullary nail having a transverse aperture through the proximal end thereof and a transverse aperture through the distal end thereof; the body of the intramedullary nail having a central axis extending between the proximal and distal ends thereof and having a cavity extending the entire length thereof along the central axis thereof for allowing the target magnet of the magnetic positioner instrumentation to be positioned within the cavity of the body of the intramedullary nail adjacent the transverse aperture through the distal end thereof and having a protuberance within the cavity thereof at a location adjacent the transverse aperture;
(b) an intramedullary nail insert for insertion into the cavity of the body of the intramedullary nail, the intramedullary nail insert including an elongated body having a proximal end and a distal end; the body of the intramedullary nail insert having a transverse aperture therethrough for alignment with the transverse aperture through the proximal end of the body of the intramedullary nail when intramedullary nail insert is inserted into the cavity of the proximal end of the body of the intramedullary nail with the distal end of the body of the intramedullary nail insert engaging the protuberance within the cavity of the proximal end of the body of the intramedullary nail so that force is transferred between the intramedullary nail insert and the intramedullary nail; and
(c) an intramedullary nail cap for fixing the intramedullary nail insert within the cavity of the proximal end of the body of the intramedullary nail.

13. Insertion handle instrumentation for use with an intramedullary nail including an elongated body having a longitudinal axis having a proximal end with an aperture therein and having an exterior surface, and with proximal locking screws for locking the intramedullary nail to bone, the insertion handle instrumentation comprising:
(a) a body having a first end and a second end, and having an aperture through the first end thereof;

(b) attachment means for gripping the exterior surface of the proximal end of the intramedullary nail to attach the intramedullary nail to the body with the aperture through the body coincident with the aperture in the proximal end of the intramedullary nail for allowing access into the aperture in the proximal end of the intramedullary nail through the aperture in the body; the attachment means being moveable between a first position for attaching the intramedullary nail to the first end of the body and a second position for releasing the intramedullary nail from the body; the attachment means having an axis for alignment with the longitudinal axis of the elongated body of the intramedullary nail when attaching the intramedullary nail to the first end of the body; and (c) control means for moving the attachment means between the first and second positions, the control means having a control member located remote from the first end of the body and offset from the axis of the attachment means for allowing the surgeon to move the attachment means to the second position and thereby release the intramedullary nail from a location remote from the first end of the body offset from the axis of the attachment means, and offset from the longitudinal axis of the elongated body of the intramedullary nail.

14. In combination, an intramedullary nail having a hollow posterior end with a threaded portion, an insert for being inserted into the hollow posterior end of the intramedullary nail, a cap with a threaded portion for being screwed into the threaded portion of the hollow posterior end of the intramedullary nail, and insertion instrumentation for inserting the insert and the cap into the hollow posterior end of the intramedullary nail, the insertion instrumentation comprising:

(a) an inner shaft having a first end for being attached to the insert so that rotation of the inner shaft will cause the insert to rotate, and having a second end; and (b) an outer shaft having a first end for being attached to the cap so that rotation of the outer shaft will cause the cap to rotate, having a second end, and having an aperture extending completely therethrough for allowing the inner shaft to extend therethrough so that the inner shaft can rotate within the aperture in the outer shaft independently of the rotation of the outer shaft.

* * * * *

UNITED STATES PATENT AND TRADEMARK OFFICE
CERTIFICATE OF CORRECTION

PATENT NO. : 6,168,595 B1
DATED : January 2, 2001
INVENTOR(S) : Durham et al.

It is certified that error appears in the above-identified patent and that said Letters Patent is hereby corrected as shown below:

Title page, item [75],
Under the inventors, Benjamin R. Shappley should be listed as Ben R. Shappley.

Claim 5,
Line 14, delete "(a)" and insert -- (b) --.

Signed and Sealed this

Fourteenth Day of August, 2001

Attest:

Attesting Officer

NICHOLAS P. GODICI
Acting Director of the United States Patent and Trademark Office